US012794881B2

(12) United States Patent
Aunger et al.

(10) Patent No.: US 12,794,881 B2
(45) Date of Patent: Nov. 10, 2026

(54) ENHANCED AUTHENTICATION TECHNIQUES USING VIRTUAL PERSONA

(71) Applicant: Health2047, Inc., Menlo Park, CA (US)

(72) Inventors: Charles Aunger, Hayward, CA (US); Roel Nuyts, Amsterdam (NL); Judy Barkal, Palo Alto, CA (US); Karl Ronn, Palo Alto, CA (US)

(73) Assignee: Health2047, Inc., Menlo Park, CA (US)

( * ) Notice: Subject to any disclaimer, the term of this patent is extended or adjusted under 35 U.S.C. 154(b) by 54 days.

(21) Appl. No.: 18/891,652

(22) Filed: Sep. 20, 2024

(65) Prior Publication Data

US 2025/0088505 A1 Mar. 13, 2025

Related U.S. Application Data

(63) Continuation of application No. 17/446,210, filed on Aug. 27, 2021, now Pat. No. 12,101,316.

(60) Provisional application No. 63/071,941, filed on Aug. 28, 2020.

(51) Int. Cl.
*H04L 9/40* (2022.01)
*G16H 10/60* (2018.01)
*H04W 8/00* (2009.01)

(52) U.S. Cl.
CPC ......... *H04L 63/0861* (2013.01); *G16H 10/60* (2018.01); *H04L 63/083* (2013.01); *H04W 8/005* (2013.01)

(58) Field of Classification Search
None
See application file for complete search history.

(56) References Cited

U.S. PATENT DOCUMENTS

| | | | | |
|---|---|---|---|---|
| 8,966,075 B1 * | 2/2015 | Chickering | H04L 63/10 709/227 |
| 10,200,364 B1 * | 2/2019 | Ketharaju | H04L 63/0853 |
| 10,505,924 B1 * | 12/2019 | Barakat | H04W 12/64 |
| 10,911,443 B2 * | 2/2021 | Rosendal | H04L 63/0853 |
| 2002/0059435 A1 * | 5/2002 | Border | H04L 45/30 709/228 |
| 2006/0021018 A1 | 1/2006 | Hinton et al. | |
| 2015/0089568 A1 | 3/2015 | Sprague et al. | |
| 2016/0166779 A1 * | 6/2016 | Tabata | G16H 10/60 705/3 |

(Continued)

OTHER PUBLICATIONS

Boukovalas et al., "Secure Multicasting", Network Security: Current Status and Future Directions, Institute of Electrical and Electronics Engineers, 2007 (Year: 2007).*

(Continued)

*Primary Examiner* — Piotr Poltorak
(74) *Attorney, Agent, or Firm* — Knobbe, Martens, Olson & Bear, LLP

(57) ABSTRACT

Systems and methods enhanced authentication techniques using virtual persona. An example method includes receiving a request associated with authorization of a user. Information identifying a virtual persona associated with the user is accessed, the virtual persona comprising meshes. Confidence measures associated with the user's identity are determined based on the meshes. The request is responded to based on the confidence measures.

18 Claims, 15 Drawing Sheets

(56) References Cited

U.S. PATENT DOCUMENTS

| | | | | |
|---|---|---|---|---|
| 2019/0052683 | A1 | 2/2019 | Logue et al. | |
| 2019/0104422 | A1* | 4/2019 | Chiang ................. | H04W 48/08 |
| 2020/0322329 | A1 | 10/2020 | Lynn et al. | |
| 2020/0413255 | A1 | 12/2020 | James et al. | |
| 2021/0058391 | A1* | 2/2021 | Graybeal .............. | H04W 12/72 |

OTHER PUBLICATIONS

Timothy Rooney, "Security Considerations", Introduction to IP address Management, Institute of Electrical and Electronics Engineers (Year: 2010).*

Passpack found at https://www.youtube.com/watch?v=QMHrbxQKG9k, author unknown, 2009 (Year: 2009).

Passpack2 "Introduction to Passpack Password Manager" found at https://www.youtube.com/watch?v=z9ISUYhWHA (Year: 2019) (Year: 2019).

* cited by examiner

ENHANCED AUTHENTICATION TECHNIQUES USING VIRTUAL PERSONA

CROSS-REFERENCE TO RELATED APPLICATIONS

This application claims priority to, and is a continuation of, U.S. patent application Ser. No. 17/446,210 titled "ENHANCED AUTHENTICATION TECHNIQUES USING VIRTUAL PERSONA" and filed on Aug. 27, 2021, the disclosure of which is hereby incorporated herein by reference in its entirety.

TECHNICAL FIELD

The present disclosure relates to systems and techniques for applications, such as web applications, for authentication. More specifically, this disclosure relates to enhanced techniques for authenticating users.

BACKGROUND

With the increasing importance of the internet, users are increasingly having to rely upon complex authentication techniques to ensure the safety of their information which is stored in systems of the internet. As may be appreciated, using different complexities of passwords is a common technique to ensure that a user's important information is not improperly accessed. For example, a user may use a first password for an important website. In this example, the first password may be substantially complex requiring the user to memorize a substantially random series of characters. Additionally, the first password may be lengthier to enter as compared to other passwords. This added complexity may reduce an extent to which an attacker may use password cracking techniques to improperly access the important website. In contrast, the user may utilize a second password for a less important website. In this example, the second password may be substantially shorter and/or less complex. The user may therefore rapidly enter this second password for the less important website, while being less concerned as to improper access by an attacker.

The above-described technique introduces technical problems in that the user may reduce the security posture for certain websites to increase the user experience associated with using the websites. Additionally, some users may avoid the practice of leveraging complex passwords in general. Instead, these users may prefer to employ one or more shorter passwords to reduce an extent to which memorizing passwords is required.

The above-described technique additionally may cause users to re-use passwords across websites. Even with a complex password, if the password is re-used across websites it may be subject to attack. For example, a website may suffer an attack by one or more malicious attackers. In this example, the malicious attackers may obtain passwords used by users of the website. If these passwords are re-used, the malicious attackers may be able to access other websites of certain of the users.

To address these problems, a user may employ tools such as password managers. These tools may store unique passwords for each of a multitude of websites used by a user. Additionally, these tools may enable the automatic generation of new passwords and allow for quickly accessing a password used for a certain website. Furthermore, these password managers may respond to biometric authentication techniques. For example, the user may be required to scan his/her face via a camera to access a password manager. As another example, the user may be required to press his/her thumb or finger on a portion of a mobile device.

The above-described biometric authentication techniques may thus serve to indicate an identity of a user. While these techniques may be subject to attacks, they provide an added security layer. A user may therefore leverage the password manager to generate unique passwords for each password. Additionally, the user may use biometric authentication techniques to reduce, or substantially eliminate, improper access to the password manager itself. However, users may find the required use of biometric authentication techniques to introduce delay. For example, the user may be required to routinely scan his/her face to access the user's passwords.

SUMMARY OF CERTAIN EMBODIMENTS

The systems, methods, and devices of this disclosure each have several innovative aspects, no single one of which is solely responsible for the all of the desirable attributes disclosed herein.

Although certain embodiments and examples are disclosed herein, inventive subject matter extends beyond the examples in the specifically disclosed embodiments to other alternative embodiments and/or uses, and to modifications and equivalents thereof.

The details, including optional details, of one or more embodiments of the subject matter of this specification are set forth in the accompanying drawings and the description below. Other optional features, aspects, and advantages of the subject matter will become apparent from the description, the drawings, and the claims.

BRIEF DESCRIPTION OF THE DRAWINGS

Throughout the drawings, reference numbers are re-used to indicate correspondence between referenced elements. The drawings are provided to illustrate embodiments of the subject matter described herein and not to limit the scope thereof.

Like reference numbers and designations in the various drawings indicate like elements.

DETAILED DESCRIPTION

Introduction

Figure 1A:
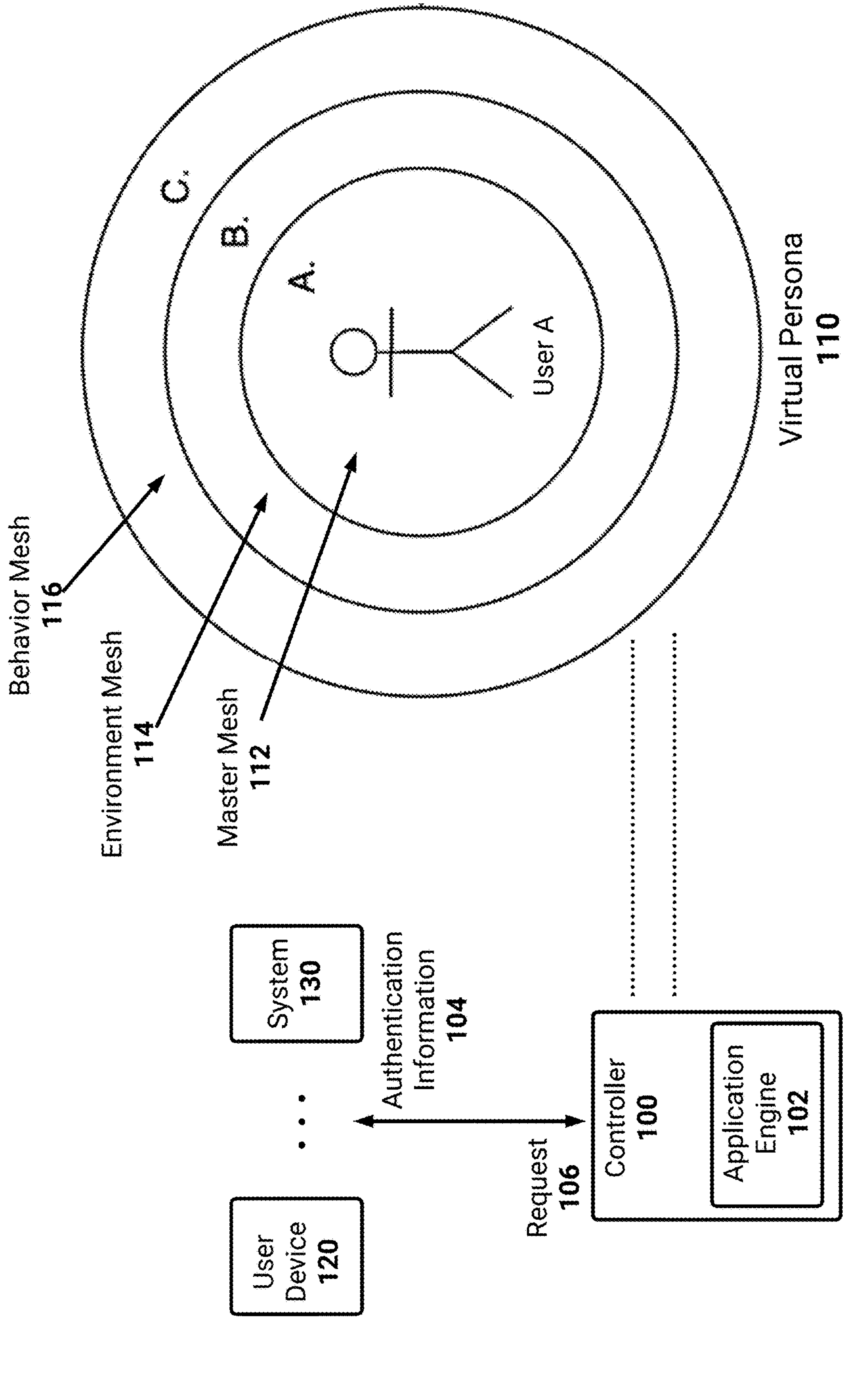
FIG. 1A illustrates an example controller maintaining a virtual persona for an example user.

This specification describes, among other things, improved authentication techniques for users. As will be described, one or more controllers which are typically carried by, or which are typically otherwise proximate to, a user may be leveraged to enhance automated authentication techniques. Example controllers may include a mobile device, a tablet, a wearable device, a laptop, a custom device, and so on. In some embodiments, a controller may represent an application or software executing on a system (e.g., a cloud system) which receives information from devices proximate to the user. Since these controllers may be typically proximate to the user, they may determine (e.g., learn) information which is usable to uniquely identify the user. For example, the controller may be utilized to determine a confidence measure associated with the user's identity. Advantageously, this confidence measure may be used to, among other things, automatically allow access to a website or system by the user.

As an example, a controller may be a user's mobile device. For this example, the mobile device may determine that when the user is at home, the mobile device is typically connected to a particular Wi-Fi network. As another example, the mobile device may determine that when the user is located at work, the mobile device is typically in wireless communication with specific printers, specific other mobile devices, and so on. Through this determined information, the controller may uniquely identify the user. Thus, and as an example, if the user attempts to access a password manager on his/her laptop, the controller may provide information to the laptop confirming that the password manager may be opened. As will be described, this may eliminate or substantially reduce an extent to which the user is required to provide a password or biometric authentication to the password manager.

Described below are example techniques which leverage the above-described controllers. As will be described, the controller may monitor different aspects of a user. These different aspects may collectively be used to represent a digital fingerprint for the user. For example, a first aspect may relate to devices which the user controls, owns, and so on. In this example, the devices may be known to be controlled or owned by the user. These devices may have particular signatures or identifiable information which may be combined (e.g., hashed) to be associated with the user. As another example, a second aspect may relate to devices which are known to be proximate to the user at different times and/or locations. In this example, the devices may include a car stereo while the user drives to work, a printer which is known to be connected to a wireless network at work, and so on. The devices for the second aspect may, in some embodiments, represent devices which are accessible, identifiable, and/or available, on networks the controller or devices associated with the first aspect are logged onto. Similar to the above, these devices may have particular signatures or identifiable information which may be combined (e.g., hashed) to be associated with the user. As another example, a third aspect may relate to behavior of the user. In this example, the controller may determine that the user's location typically follows a particular location pattern as the user drives to work. The controller may also determine that the user's mobile device typically connects to a Bluetooth car stereo as the user drives to work. This behavior information, which may relate to location and/or time, may similarly be associated with the user.

The above-described confluence of information may be monitored by the controller. In this specification, the information may be referred to as a 'virtual persona' for the user. Additionally, the different aspects may be referred to herein as meshes. The virtual persona may thus be associated with one or more meshes. An example mesh includes a master mesh which is associated with devices the user controls or owns. Another example mesh includes an environment mesh which is associated with devices known to be proximate or present in the user's environment. Another example mesh includes a behavior mesh which is associated with behavior patterns or characteristics of the user.

Based on these meshes, a confidence or confidence measure may be determined which indicates a confidence of an identify of the user. For example, a controller may detect that a person is proximate to a set of devices known to be used by the person (e.g., in the morning). In this example, the controller may detect that the person enters a car which has a Bluetooth stereo known to be associated with the person. Additionally, the controller may detect that the person travels to a work location known to be associated with the person. Optionally, while traveling to work the controller may detect Wi-Fi access points known to be on the route to work (e.g., based on historical information). Furthermore, the controller may detect that while at work the person uses devices known to be associated with the person and/or that devices known to be commonly placed at work (e.g., printers) are detectable.

Thus, based on the above information, if the person tries to log into his/her laptop while at work, authorization may be granted without requiring a password. For example, and as will be described, the laptop may receive information from the controller indicating the confidence is greater than a threshold. As another example, the laptop may receive information from a controller which is a cloud agent executing on a cloud system indicating that the confidence is greater than a threshold.

Advantageously, one or more policies may be configured where a user can access specific information, be allowed into specific devices and/or websites, based on respective threshold confidences being met. In some embodiments, a confidence may relate to a number of features of a digital fingerprint which are available or have been detected. For example, a feature may relate to a device known to be associated with a user. As another example, a feature may relate to behavior information of the user. Thus, these features may be aggregated and used to determine a confidence. If the confidence is high (e.g., 100%, 95%, and so on), a user may b allowed full access to websites, digital files, and so on. However, if the confidence is under that then the user may be allowed access to files which have a different (e.g., lower) security rating. If the confidence is too low, such as 50%, 45%, 60%, then the user may be required to authenticate (e.g., to the controller, such as his/her smart phone), using biometric authentication, entry of a password, and so on.

The description below focuses on use of a controller to monitor and/or maintain a virtual persona for a user. In some embodiments, the user may have a multitude of controllers. For example, there may be a controller at the user's work, a different controller at the user's house, and so on. These controllers may pass information between them such that they may form a more complete picture or fingerprint of the user. For example, the controllers may store information in cloud storage accessible to the other controllers. As another example, the controllers may store information in a mobile device carried by the user. Thus, the mobile device may receive, or transmit, information to other controllers.

Introduction—Authentication Techniques

It may be appreciated that a user may have a plethora of passwords which are used for different websites, systems, platforms, and so on. For example, the user may be a medical professional who uses an electronic medical record (EMR) system through his/her workday. In this example, the user may be required to provide authentication information to the EMR system. Example authentication information may include a username and password, biometric authentication information, a keycard or badge, and so on. Thus, the user may be required to input authentication information prior to accessing the EMR system.

The above-described authentication information may be used to confirm that the user is who they say they are. That is, the authentication information may be indicative of an identity of the user who is attempting to access the EMR system. Indeed, a password may be assumed to be known by only the user. Thus, if the EMR system receives the password then the system may allow access based on the assumption in the user's identity.

As described above, however, a password may be improperly obtained by a malicious actor. Thus, it may be advantageous to add an extra layer of security onto solely requiring a password. Different techniques may be employed for this extra layer. As an example, when the user provides his/her password to the EMR system, the user's mobile device may receive information identifying a unique number. For example, the unique number may be provided as a text message to the mobile device or may be presented via an application executing on the user device. This added technique, known as two-factor authentication, may allow for an increase in the confidence in an identity of the user. For example, it is more likely that the user is a specific person if they both (1) know the person's password and (2) have access to the person's password.

Additionally, or alternatively to the above, biometric authentication may be used to increase the confidence in an identity of the user. For example, a camera may obtain an image of the user's face. The resulting image may be analyzed to determine whether it reflects a specific person. As an example, a neural network may be used generate an encoding of the face into a learned vector space. A distance metric may be computed between the encoding and encodings known to be associated with specific persons. In this way, a person who corresponds to the face in the photo may be identified. Additional biometric authentication may include a thumbprint, fingerprint, voice signature, and so on.

These authentication techniques may thus be leveraged to enhance security of the EMR system. Similarly, the authentication techniques may be used to allow for access to web pages. As an example, a password manager may be used on a user device of a user. Similar to the above, the user may attempt to access the password manger. In response, the password manager may require a password, two-factor authentication, biometric authentication, and so on.

While these authentication techniques may provide for added assurance regarding the identity of a user who is attempting to access a system or software, they require additional set up, effort by users, and so on. For example, the above-described authentication techniques may require additional user input. In this example, the user input may include identifying, and then entering, a unique code with respect to two-factor. The user input may also include selecting an option and then providing biometric authentication. These added steps may be cumbersome to users and increase a time until the users can access systems or software. Thus, they may not be less commonly used than would be advantageous.

Introduction—Virtual Persona

In contrast to the above-described authentication techniques, a virtual persona may be maintained for a user. The virtual persona may be associated with information usable to uniquely confirm an identity of the user. For example, and as may be appreciated, a person may typically have certain states in his/her daily life. Example states may include being at home, being at work, being in transit (e.g., commuting), engaging in weekend activities, engaging in vacations, and so on. For each state there may be a combination of features or information which can be used to determine an identity of a corresponding person.

As an example with respect to being at home, a person may typically use a set of devices while at home. As an example, the person may typically access a specific mobile device to perform certain actions (e.g., read the news, message friends, and soon). As another example, the person may typically activate a smart television (TV) device to watch streaming media, television, and so on. As another example, the person may typically wear a specific wearable device (e.g., smart watch) while in his/her home. As another example, the person's mobile device may be in communication with certain smart speakers, an intelligent personal assistant executing on a smart speaker, and so on.

In the above-described example, the collection of devices may be used to uniquely identify the person. For example, it may be unlikely that a different person may have access to a same mobile device. In this example, the mobile device may be identified based on unique identifying information such as a media access control (MAC) address, an international mobile equipment identity (IMEI) code, and so on. For example, a hash of the identifying information may be stored. Additionally, it may be even less likely that a different person may have access to the same mobile device and also access to the same smart TV device, specific wearable device, and so on. Thus, if all of these devices are determined to be proximate to a person, then a reasonable determination that the person corresponds to a specific identity may be effectuated.

In addition to devices, further information may be used to increase a confidence in the above-described person's identity. For example, behavior of the person may be monitored over time. In this example, and as will be described in FIG. 1D, the person may typically follow a certain schedule. An example schedule may include the person being at home from certain hours of the day (e.g., 6pm to 8 am). While the person is at home, the person may use the devices described above. The example schedule may then indicate that the person drives to work, takes the subway to work, and so on. During this commute, the person may be proximate to devices which are substantially similar across different days. For example, the person may be proximate to a car stereo which is uniquely identifiable. As another example, the person may be proximate to a Wi-Fi access point which is uniquely identifiable via an access point name (APN). As another example, during the commute the person's location may adjust. For example, the person's mobile device may record changing locations. As another example, the person's mobile device may connect to different cell towers as the location changes.

In the above-example, a person who is following that behavior, which includes the above-described identifiable devices, may be determined to correspond with a specific identity very accurately. Indeed, and as may be appreciated, as the features of a person are more closely monitored, a confidence in the person's identity may be increased.

The above-described information may thus form a virtual persona for the person and be monitored by one or more controllers associated with the person. For example, and as described above, a controller may represent a mobile device used by the person. The controller may execute an application which enables the gathering and monitoring of at least the above-identified information. Thus, when the person attempts to access a system or software, the controller may automatically provide authentication information to the system or software. With respect to the EMR system described above, the controller may provide authentication to the EMR system via a wireless or wired connection. Since the controller monitors the virtual persona, the controller may determine to a substantially high confidence metric that the person is authorized to use the user account for the EMR system.

The application on a user's smart phone, as an example, may allow for associating devices and information with the user. For example, a device known to be associated with the user may display a graphical code (e.g., a QR code). In this example, the device may execute an application or be accessing a website associated with the techniques described herein. For example, a cloud system may cause presentation of the QR code. The application may scan the QR code and then associate the laptop with the user. In some embodiments, the application may cause a hash of the QR code information and/or identifying information associated with the laptop to be stored (e.g., by the application, by a cloud component in communication with the application). In this way, certain 'master' devices known to be used or owned by the user may be associated with the user. As described above, each device may represent a feature. An aggregation of these features, such as a threshold amount, may be used to identify an identity of the user (below referred to as a 'master mesh'). As an example, the aggregated amount may represent an amount which is presently proximate to the smart phone, or which were proximate within a threshold amount of time or at respective times known to be commonly proximate to the smart phone.

Introduction—Example Technical Advantages

This application therefore addresses technological problems and improves upon prior techniques for authentication. Prior authentication techniques, such as two factor or biometric authentication, required user input which users may find cumbersome to provide. This may result in low adoption for these prior authentication techniques. Instead, users may prefer to use insecure passwords for systems, software, web pages, and so on. In contrast, the techniques described herein may enable substantially seamless authentication to systems, software, web pages, and so on. For example, a controller may provide authentication information to the systems, software, web servers associated with the web pages, and so on. Advantageously, the controller may optionally be hosted online (e.g., via a cloud platform). In this way, the controller may directly interface with web servers.

Historically, identification and therefore authentication for role-based permissions has been tied to organizations. A person would have as many identities as organizations he/she belongs to or services he/she uses. However, identity by its definition may not be a plural concept but rather singular. A person may therefore only have one unique identity. The relationship between that unique identity and an organization/service should describe the roles and permissions. Thus, identity may be singular but relationships with their own particular permissions may be plural.

In this way, the above-described person may be uniquely identified by a controller based on the person's virtual persona. This virtual persona may allow for access to arbitrary systems. In certain embodiments, the controller may allow for providing a username and password associated with a user account the person has. In these embodiments, the controller may therefore provide, at least, for an enhanced password manager.

In other embodiments, the controller may provide confirmation information to systems, software, web servers, and so on regarding an identity of a person. This confirmation information may enable the software, web servers, and so on, to access a user account associated with the person. In these embodiments, the person's identity may therefore function as his/her password. For example, the controller may confirm that the person who is attempting to access a web page corresponds to a particular user identity based the person's virtual persona. In this example, the controller may then provide confirmation information identifying the particular user identity to a web server associated with the web page. Therefore, this application describes future-facing techniques which move beyond username, password, and so on, and instead rely upon the person's identity itself.

Example Block Diagrams

FIG. 1A illustrates an example controller 100 maintaining a virtual persona 110 for an example user. The controller 100 may be in communication with one or more user devices (e.g., user device 120), systems (e.g., server system 130), and so on. In the illustrated embodiment, the example user is 'User A," and the example user is associated with a virtual persona 110 comprising one or more meshes. Example meshes, which are described in more detail below, may include a master mesh 112, an environmental mesh 114, and a behavior mesh 116. As described herein, each mesh may be associated with example information associated with the example user. The example information may be used to confirm an identity associated with the example user. For example, when the example user attempts to access an application, software, a system, and so on, the virtual persona may be used to confirm an identity of the user.

The controller 100 may represent a user device which is proximate to the example user. For example, the controller 100 may be a mobile device of the user. In this example, the mobile device may represent a smart phone which the user uses to make calls, access web pages, execute mobile applications and so on. As another example, the controller 100 may be a tablet of the user. In this example, the tablet may commonly be carried by the user, or otherwise proximate to the user, while at home, while commuting, while at work, and so on. As another example, the controller 100 may be a laptop of the user. Similar to the above, the laptop may be a device which is commonly used, and/or typically proximate to, the user. As another example, the controller 100 may be a wearable device which is typically worn by the user. For example, the wearable device may be a smart watch which is typically worn on the user's wrist or otherwise typically proximate to the user.

In some embodiments, the controller 100 may be a custom device which is utilized to maintain a virtual persona 110. For example, the controller 100 may include one or more processors and may allow for wireless or wired communications. Example wireless communications may include Bluetooth, Wi-Fi, infrared communications, satellite communications, radio or cellular communications, and so on. Additionally, the controller 100 may include one or more global navigation satellite system (GNSS) receivers. In this way, the controller 100 may be used to determine a present location of the controller 100.

The controller 100, additionally, may represent an agent executing on a cloud system. The controller 100 may receive information from one or more application executing on user devices associated with the example user. In some embodiments, these devices may represent some, or all, of the devices associated with the master mesh 112 described herein.

FIG. 1A illustrates the controller 100 including an application engine 102. With respect to a mobile device, the mobile device may obtain a particular application from an online application store (e.g., an 'app'). The example user may then use the application to establish the mobile device as a controller 100. For example, and as will be described, the mobile device may establish the virtual persona 110. In this example, the mobile device may obtain information identifying devices of the example user which are typically proximate to the user. The user may also add one or more other users with which the user has a relationship. For example, the user may add his/her roommate or friend as a relationship. As will be described, these other users may be used to enhance the virtual persona 110 of the example user. Additional description regarding establishing a virtual persona 110 is included below, with respect to FIGS. 4A-4B.

The application engine 102 may also represent software executing on a laptop or computer. In some embodiments, the application engine 102 may represent a password manager which allows for storage of passwords used by different web servers, software, systems, and so on. In contrast to prior password managers which may have relied upon entering a lengthy password to access the stored passwords, or providing biometric authentication information, the application engine 102 may automatically enable access to a passenger based on the virtual persona 110.

The application engine 102 may enable the establishing and maintaining of the virtual persona 110. As an example, the application engine 102 may access wireless communication functionality of the controller 100. Using this functionality, the application engine 102 may identify devices which are in communication with the controller 100. For example, the application engine 102 may allow for connecting to different Wi-Fi or Bluetooth connections. In this example, and as will be described, the application engine 102 may identify devices which are responsive to network requests from the engine 102. In this way, the application engine 102 may identify devices connected to a particular Wi-Fi network.

The application engine 102 may also determine a location of the example user at different times. As will be described, the application engine 102 may associate certain devices, behavior, and so on, of the example user with different locations. These devices, behavior, and so on, may be associated with the virtual persona of the example user. In some embodiments, the application engine 102 may access personal information of the example user. For example, the application engine 102 may optionally have access to a calendar of the user. In this example, the engine 102 may determine times at which the user is expected at different locations. As another example, the application engine 102 may optionally have access to other information (e.g., social network profile, emails, messages, and so on).

In all situations in which the controller 100 accesses location information and/or personal information of the user, the user may toggle such access on or off. For example, and with respect to the controller 100 being a mobile device, the example user may adjust settings of the application engine 102. These settings may allow for adjusting access rights of the application engine 102. Additionally, location and/or personal information may be encrypted, anonymized, and so on. In some embodiments, the location and/or personal information may be maintained locally on the controller 100. Additionally, the maintained information may be stored in a trusted element or may be encrypted using information from a trusted element of the controller 100.

The controller 100 may use the virtual persona 110 described herein to determine whether the example user is authorized to access software, applications, devices, or systems. For example, the controller 100 may receive a request 106 associated with accessing an application. As may be appreciated, prior techniques to access the application may rely upon the example user providing a username and password associated with the application. For example, the example user may type in the username and password directly into the application. As another example, the example user may prefer to access a web page and may interact with a password manager to cause inclusion of a username and password onto the web page.

In contrast to the above, the controller 100 may respond to the request 106 based on the virtual persona 110 described herein. For example, the controller 100 may determine one or more confidence metrics (also referred to herein as confidence measures) associated with an identity of the example user. As will be described, these may be based on the meshes 112-116 described above. As an example, the controller 100 may determine that a threshold number of devices which are known to be controlled or used by the user are proximate to the user (e.g., presently, within a threshold period of time, and so on). As another example, the controller 100 may determine, based on a location of the controller 100, that a threshold number of devices which are known to be at the location are detectable. As another example, the controller 100 may determine that a behavior of the example user matches known behavior profiles or patterns of the example user.

Thus, the controller 100 may determine a certainty associated with an identity of the example user. For example, and with respect to accessing an application, the controller 100 may determine that an identity of a person who is attempting to access the application is known with a particular confidence. In this example, the controller 100 may determine confidence metrics or measures based on the virtual persona.

If these confidence metrics or measures exceed one or more thresholds, then the controller 100 may allow access.

As illustrated, the controller 100 has allowed access by providing authentication information 104 in response to the request 106. With respect to the application engine 102 representing a password manager, the authentication information 104 may represent a username and password. Advantageously, since the controller 100 is monitoring the virtual persona 110, the username and password may be provided automatically upon receipt of the request 106.

The authentication information 104 may, as illustrated, additionally be provided to a user device 120. For example, the user device 120 may represent a computer or laptop on which the example user is working. As an example, the user device 120 may be used as an electronic medical record (EMR) system. Thus, the controller 100 may allow for access to the EMR system without requiring the example user to enter a password, provide biometric authentication, provide a radio-frequency identification (RFID) keycard, and so on.

With respect to a system 130, the authentication information 104 may be utilized to allow access to the system 130 by the example user. As an example, the system 130 may represent a web server. In this example, the controller 100 may allow for the example user to access the web server automatically. Optionally, the controller 100 may receive information from a user device on which the example user is working. For example, the controller 100 may represent a mobile device of the user. The user may be using a laptop to access the web server. In this example, the laptop may provide the request 106 to the controller 100 and the controller 100 may automatically provide authentication information 104 to the web server. This may allow the laptop to access the web server in a seamless manner.

Optionally, the controller 100 may receive the request 106 directly from the web server. For example, a web page associated with the web server may include a selectable option associated with logging in via virtual personas. In this example, the user may select this option and the web server may cause information to be provided to the controller 100. As will be described below, with respect to at least FIG. 3, the controller 100 may be responsive to an online agent or application which is executing in a cloud platform. Thus, the web server may provide information to this online agent, which may then provide a request 106 to the controller 100. The controller 100, as described above, may determine whether to authorize the request 106 based the virtual response. In this way, web servers or other outside systems may enable use of virtual personas.

Optionally, the online agent may function as the controller 100 and may directly monitor the virtual persona 110. For example, the online agent may receive information from example devices and systems which are known to be controlled or used by the example user. In this example, the devices and systems may execute respective applications or software (e.g., the application engine 102). The online agent may then intercept or receive (e.g., via daemons) the request 106. For example, if the user attempts to log into a laptop, the laptop may route the request 106 to the online agent.

In some embodiments, the request 106 may be associated with a priority or access level. For example, a weather application may require less confidence in the example user's identity. In this example, the controller 100 may therefore provide authentication information 104 based on one or more confidence metrics or measures exceeding a first threshold. This may represent, as an example, that a threshold number of features (e.g., devices) are proximate to the user which are known to be controlled or owned by the user. As another example, a banking application may require a greater confidence in the example user's identity. In this example, the controller 100 may provide authentication information 104 based on the one or more confidence metrics or measures exceeding a second threshold which is higher than the first threshold. This may represent, as an example, that a threshold number of devices are proximate to the user which are known to be controlled or owned by the user. This may also represent that a threshold number of specific devices are present at a location of the user. This may also represent that the user's current, or recent, behavior matches a behavior profile.

If the controller 100 determines that the confidence metrics or measures are less than one or more thresholds, the controller 100 may require that the example user provide additional information. For example, the controller 100 may detect two devices which are known to be owned or controlled by the user. In this example, the controller 100 may require three devices be detectable for the example user. As an example, three devices may have been determined to be typically proximate to the user (e.g., while at a particular location). The controller 100 may therefore require that the user provide biometric authentication. For example, the user may be required to scan his/her face via the controller 100. As another example, the user may be required to scan his/her face via a device which is known to be controlled or owned by the user. Additional description related to providing additional information is included below, with respect to FIG. 6.

Figure 1B:
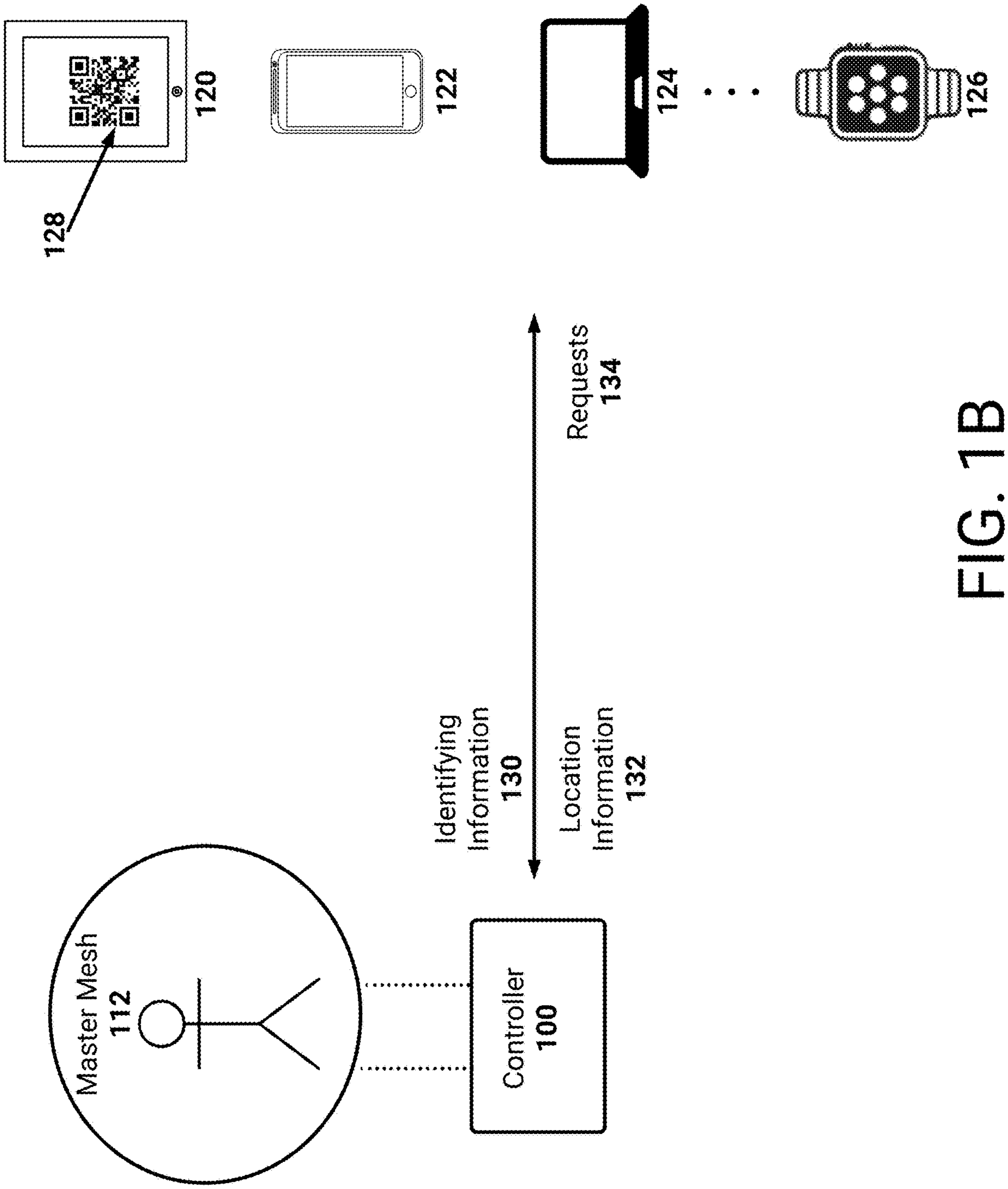
FIG. 1B illustrates the example controller maintaining an example master mesh associated with the virtual persona.

FIG. 1B illustrates the example controller 100 maintaining an example master mesh 112 associated with the virtual persona 110. The master mesh 112 may be generated by the controller 100 and may include devices which are owned or controlled by the user. Example devices are included in FIG. 1A, and may include a tablet 120, a mobile device 122, a laptop 124, a wearable device 126, and so on.

It may be appreciated that devices or systems may be associated with unique identifying information. For example, a mobile device may be associated with an international mobile equipment identity (IMEI) code. In this example, the IMEI code may be assigned by a manufacturer of the mobile device. This number may therefore represent a substantially fixed identifier for the mobile device. As another example, a media access control (MAC) address may be associated with the mobile device. This number may represent a unique identifier assigned to a network interface controller of the mobile device. An additional unique identifier may include a serial number assigned to the mobile device by a manufacturer. Similarly, a laptop, smart TV device, wearable device, and so on, may be associated with such unique identifying information. One or more of these identifiable strings may be used to identify an associated device by the controller 100. In some embodiments, these identifiable strings may be hashed and stored by the controller 100.

The devices 120-126 illustrated in FIG. 1B may, as described above, be determined to be owned or controlled by the example user. In some embodiments, the user may expressly indicate that the devices 120-126 are to be used for the master mesh 112.

As an example, the controller 100 may present information to the user (e.g., via an interactive user interface) requesting that the user identify devices owned or controlled by the user. In this example, the controller 100 may optionally detect devices which are proximate to the controller 100. For example, the controller 100 may detect devices which are on a same Wi-Fi connection as the controller 100. As another example, the controller 100 may detect devices which are in wired communication with the controller 100 (e.g., on a same local area network). As another example, the controller 100 may detect devices which respond to wireless communications from the controller 100. For example, the controller 100 may identify devices on a same Wi-Fi network via providing network requests (e.g., pinging) addresses associated with a subnet. Upon detecting devices, the user may indicate which of the devices are controlled or owned by the user.

In the illustrated example, the controller is providing requests 134 to the devices 120-126. These requests 134 may be network requests provided to discover the devices 120-126. In response, the controller 100 may receive identifying information 130. As described above, the identifying information may represent IMEI codes, MAC addresses, and so on. Additionally, the controller 100 may receive location information 132 for the devices 120-126. The location information 132 may be analyzed to ensure that it matches with a location of the controller 100. Furthermore, the location information 132 may be used to determine locations at which the devices 120-126 are typically proximate to the user.

In some embodiments, the controller 100 may cause presentation of a visual identifier via each of the devices 120-126. For example, the tablet 120 in FIG. 1B is illustrated as presenting a QR code 128. In this example, the controller 100 may cause the tablet to output the QR code 128. Optionally, the tablet 120 may execute an application associated with the controller 100. For example, the tablet 120 may execute a mobile application associated with a virtual persona (e.g., the application engine 102). The mobile application may determine that the controller 100 is adding devices to the master mesh and present the QR code 128 in response. The user may also use a user interface associated with the application and cause presentation of the QR code 128.

The QR code 128 may optionally depict information usable to identify the tablet 120. For example, the QR code 128 may be generated based on a unique identifier of the tablet 120 (e.g., an IMEI code). The QR code 128 may also be generated based on the unique identifier, a current time stamp, and a location of the tablet. The location may be determined based on a GNSS sensor included in the tablet 120. The controller 100, for example a mobile device, may then use a camera to obtain an image of the tablet. The QR code 128 may be analyzed and the controller 100 may verify the time stamp and location.

The QR code 128 may therefore allow for rapidly adding devices to the master mesh 112. Additionally, the QR code 128 may ensure that the devices are located at a same location as the user. In this way, the controller 100 may limit a potential actor vector in which devices may be improperly included in the master mesh 100.

The devices 120-126 may be used by the controller to maintain the master mesh 112. For example, the controller may monitor for times at which the devices 120-126 are detected. In this example, the controller 100 may generate a profile associated with times at which the devices 120-126 are proximate to the user. Additionally, the controller 100 may determine locations at which the devices 120-126 are typically proximate to the user.

As will be described, the controller 100 may authenticate the user for a device, system, application, and so on, based at least in part on detecting a threshold number of the devices 120-126 as being proximate to the user. For example, the user may prefer to log-into a website. In this example, the controller 100 may identify a number of the devices 120-126 which are near the user. An increasing number of these devices may represent a greater signal, or information, with respect to the user's identity. For example, if all of the devices 120-126 are present then it is more likely that the user corresponds to a correct real-world person. In contrast, if none of the devices 120-126 are present then it may provide a signal that the person attempting to access the website is not the correct real-world person.

Figure 1C:
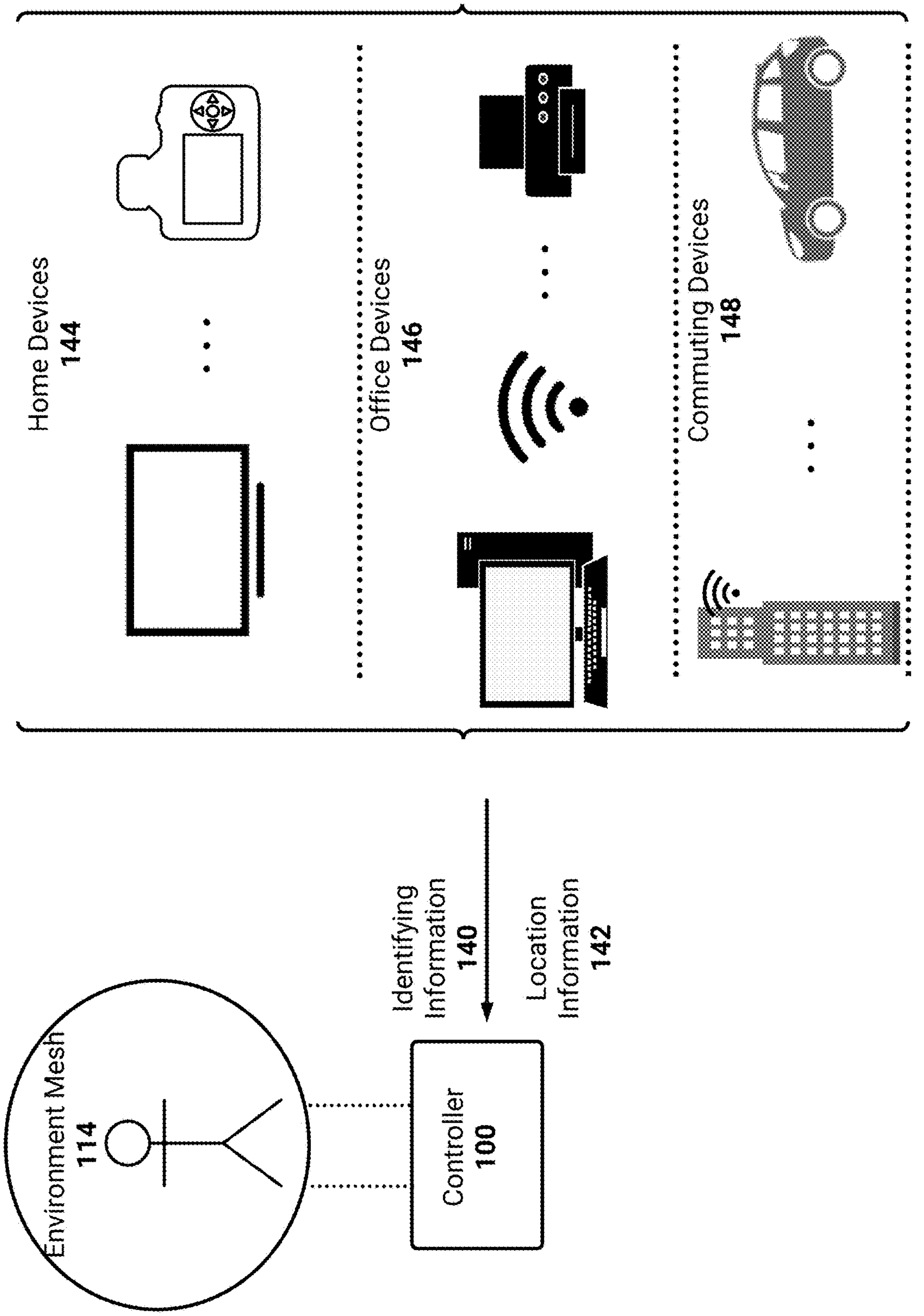
FIG. 1C illustrates the example controller maintaining an example environment mesh associated with the virtual persona.

FIG. 1C illustrates the example controller 100 maintaining an example environment mesh 114 associated with the virtual persona 110. The illustrated example includes a multitude of devices which may be located at different locations the user typically visits. These devices may be distinct from the devices 120-126 in FIG. 1B. For example, these devices may represent devices which are present in a direct environment of the user. The controller 100 may store information 140 identifying these devices, such as IMEI codes, MAC addresses, or other device identifiers as described herein. The information 140 may represent hashed versions of the IMEI codes, MAC addresses, or other identifiers. As will be described, these devices may allow for a further drilling down into a fingerprint associated with the user. As an example, these devices may be typically fixed at different locations and therefore may represent indicia of the user's identity while the user is at the different locations. In this way, the controller 100 may store location information 142 associated with the devices.

In FIG. 1C, example home devices 144 are included. These home devices 144 may be separate from the devices 120-126 of FIG. 1B and may indicate devices which are identifiable by the controller 100 at the user's home (e.g., via a home network). For example, a television is illustrated in the embodiment. It may be appreciated that televisions may typically be configured to connect to home Wi-Fi networks. Thus, the controller 100 may detect the existence of the television. Additionally, the home devices 144 include a camera. Similarly, modern cameras may be responsive to wireless communications. For example, the cameras may include Bluetooth functionality. As another example, the cameras may include Wi-Fi functionality.

The home devices 144 may thus be detected by the controller and included in the environment mesh 114. Advantageously, these home devices 144 may be associated with the home location by the controller 100. Thus, the controller may store information indicating that the devices should be, or have been known to be, located at the user's home. In some embodiments, the controller 100 or a mobile device used by the user may request that the user confirm the location. For example, the controller 100 may indicate that the user confirm that the television and camera are to be included in the environment mesh. The user may then confirm that the television and camera are associated with the user's home.

FIG. 1C further includes example office devices 146. These office devices may be detected via the controller 100 while at the user's office. With respect to the controller 100 being a mobile device of the user (e.g., executing an application), the mobile device may connect to a Wi-Fi network while at work. This connection may allow for the mobile device to identify devices which are located at the user's office. For example, and as illustrated, the example office devices 146 include a work computer, a Wi-Fi access point, and a printer. With respect to the Wi-Fi access point, the controller 100 may store information identifying the access point. Example information may include an access point name (APN). In addition to Wi-Fi, the controller 100 may detect devices which are in local wireless communication (e.g., Bluetooth).

Similar to the home devices 144, the controller may associate the office devices 146 with the location of the office. In this way, the controller 100 may store information identifying that while at work, the controller 100 should be able to detect at least a threshold number of these devices 146. As may be appreciated, such devices may be swapped in or out of the office. Thus, the controller 100 may optionally periodically or continually update the office devices 146 which form part of the environment mesh 114.

FIG. 1C further includes example commuting devices 148. These devices 148 may be detected by the controller while the user is commuting to work. In the illustrated example, an office building is illustrated. The office building may include one or more Wi-Fi access points, which may broadcast access point names. If the user drives, walks, or takes a train, past the office building, the controller 100 may store information identifying these access point names. The commuting devices 148 further includes a vehicle which may be used by the user to drive to work. The vehicle, for example, may include a stereo which allows for Wi-Fi or Bluetooth connection. Thus, the controller may store identifying information for this stereo. While not illustrated, there may be a plethora of other devices which may form part of the commuting devices 148. For example, the devices 148 may include an electric bike which is responsive to Bluetooth. The devices 148 may further include city-owned Wi-Fi access points, Bluetooth signatures associated with devices which may be substantially fixed in store windows, residences, and so on.

Similar to the above home devices 144 and office devices 146, the controller 100 may associate the devices with respective locations. For example, the controller 148 may store information associating the access point name of the office building's Wi-Fi with the location of the office building.

The controller 100 may detect the devices 144-148 described above over time. For example, the environment mesh 114 may take days, weeks, and so on, to establish by the controller 100. In contrast, the devices of the master mesh 112 described above may be rapidly added by the user. Since the controller 100 may add the devices 144-148 via detecting the devices, the controller 100 may learn which devices should be included in the environment mesh. For example, the controller 100 may require that a device is consistently at a same location, or within a threshold radius, over a threshold number of days. As another example, the controller 100 may filter devices to ensure that the environment mesh includes reliably present devices.

In some embodiments, the controller 100 may select devices for inclusion in the environment mesh based on a type of the device. For example, the controller 100 may prefer to include devices which are likely to be reliably fixed. In this example, a printer or Wi-Fi name may be considered as reliably fixed. In contrast, a mobile device being used by a different person on a subway may not be considered reliably fixed. However, the controller 100 may prefer to select the mobile device based on identifying that the different person typically rides a same subway train as the user. In this way, the controller 100 may determine that the mobile devices provide reliable information indicating that the user is following a normal course of his/her workday.

Thus, the controller 100 may determine the existence of substantially fixed in place devices which may be leveraged to determine a confidence in the user's identity. For example, the user may be determined to be located at work. In this example, the location may be determined using the controller 100 or a device included in the master mesh 112 (e.g., the user's mobile device, wearable device, and so on). The controller 100 may therefore determine which devices included in the environment mesh 114 are detectable. If greater than a threshold number of devices are detectable, then a confidence in the user's identity may be increased. As an example, these devices 146 may form part of a fingerprint for the user which uniquely identifies the user. Thus, detection of the devices 146 may lend further credence to the user's identity corresponding to a correct real-world person. In contrast, if these devices 146 are not detected, then the controller 100 may determine less confidence in the user's identity.

Figure 1D:
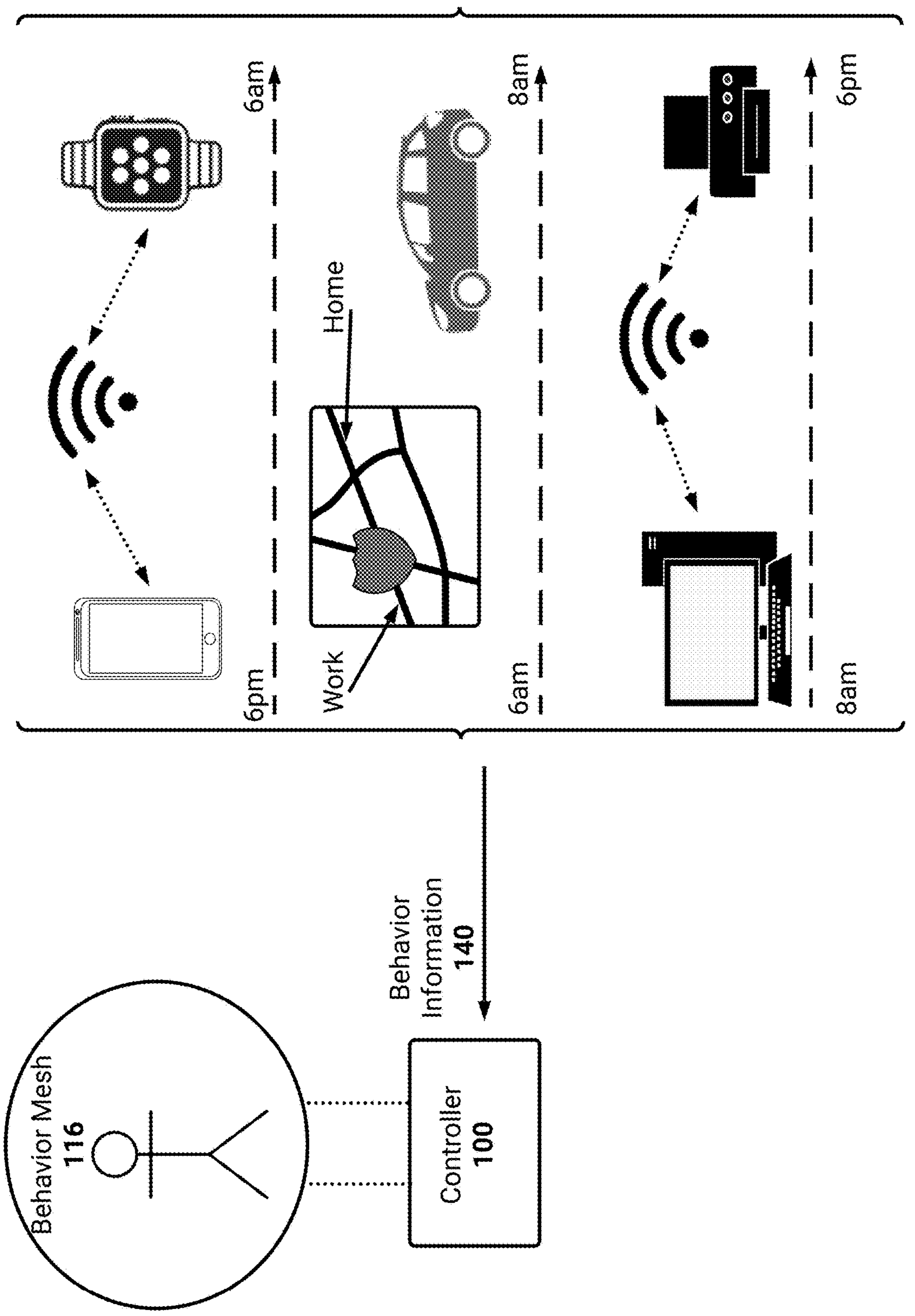
FIG. 1D illustrates the example controller maintaining an example behavior mesh associated with the virtual persona.

FIG. 1D illustrates the example controller 100 maintaining an example behavior mesh 116 associated with the virtual persona 110. The controller 100 may generate the behavior mesh 116 based on learning common behaviors of the user. For example, the controller 100 may monitor location information of the user to determine that he/she commonly leaves for work, and then travels to work along certain routes, at particular times. As another example, the controller 100 may monitor which devices the user connects to or which devices the user near while performing common behaviors.

As an example, the controller may determine that a particular time (e.g., 8 AM), the user is typically at home. To effectuate this determination, the controller may identify that a device of the user (e.g., in the master mesh 112) is connected to a Wi-Fi router known to be in the user's home. For example, the Wi-Fi router may have a specific access point name known to the controller 100. Additionally, the access point names of one or more neighbors may be further known to the controller 100. Optionally, average signal strength associated with the networks may be determined by the controller 100. The controller 100 may further store information indicating that on the user's network, there is a smart thermostat, a smart speaker, a printer, the user's partner's mobile device, and so on.

In the above-described example, the controller 100 may include this information in a known behavior for the user (e.g., also referred to as a behavior pattern). For example, the controller 100 may determine a consistency in the behavior. In this example, the behavior may include the user having a device connected to his/her Wi-Fi the neighbors Wi-Fi being detectable, the smart thermostat being detectable, and so on. This behavior may reflect behavior of the user at a certain time, such as at 8 AM, or at a certain time range (e.g., 6 PM to 8 AM).

Similarly, the illustrated example includes behavior information 140 of the user. For example, from 6 PM to 6 AM the controller 100 has determined that the user has a mobile device and wearable device which are connected to a home Wi-Fi router. As described above, the controller may further detect other Wi-Fi routers, average signal strength, and so on.

From 6 AM to 8 AM the controller 100 has determined that the user initiates a commute from the user's home to the user's work. The behavior mesh 116 may thus reflect that during this time the user is expected to be in movement along one or more known paths to the user's work. Location information may be obtained for the user via the controller, or a device included in the user's master mesh 112. Additionally, the behavior mesh 116 may indicate that during this commute the user is expected to be in a certain vehicle. This vehicle may be detected, for example by the controller 100 or a device in the master mesh 112, via a Bluetooth connection or USB connection to the vehicle (e.g., the stereo).

From 8 AM to 6 PM the controller 100 has determined that the user is located at work. During this time, the controller 100 has determined that a work PC and a printer are detectable by the controller. The work PC and printer may be connected to a Wi-Fi access point located at the user's work, which has a known access point name. While not illustrated, the controller 100 may additionally monitor keycards or Bluetooth badges worn by the user. Thus, the controller 100 may determine that the user is carrying a Bluetooth badge which is known to provide access to rooms in which certain devices are fixed (e.g., printers, scanners, and so on).

Optionally, the controller 100 may determine whether the user has logged-onto the work PC. For example, the work PC may be a legacy device which does not allow for logging-in via a virtual persona 110. In this example, the work PC may execute software or an application which may communicate with the controller 100 or a device included in the master mesh 100. As an example, the software or application may provide a wireless or wired communication to the controller 100 or device (e.g., to an application on the controller 100 or device). In this way, the controller 100 may determine that the user has successfully provided a username and password to the work PC.

It may be appreciated that the above-described behavior mesh 116 may therefore build off of the information included in the master mesh 112 and environment 114. The behavior mesh 116 may include information which is more complex and describes the user in more detail. Thus, the controller 100 may determine an increased confidence in the user's identity based on the user satisfying one or more known behaviors. For example, it may be substantially impractical and difficult for a malicious attacker to follow the sequence of behaviors described in FIG. 1D. Thus, when the user attempts to log-into an application, system, web server, and so on, the controller 100 may determine that one or more confidence metrics associated with the user's identity are high.

In some embodiments, the controller may determine measures associated with conformance to a behavior pattern. For example, the controller may determine deviations from a behavior pattern and thus reduce a measure.

Figure 1E:
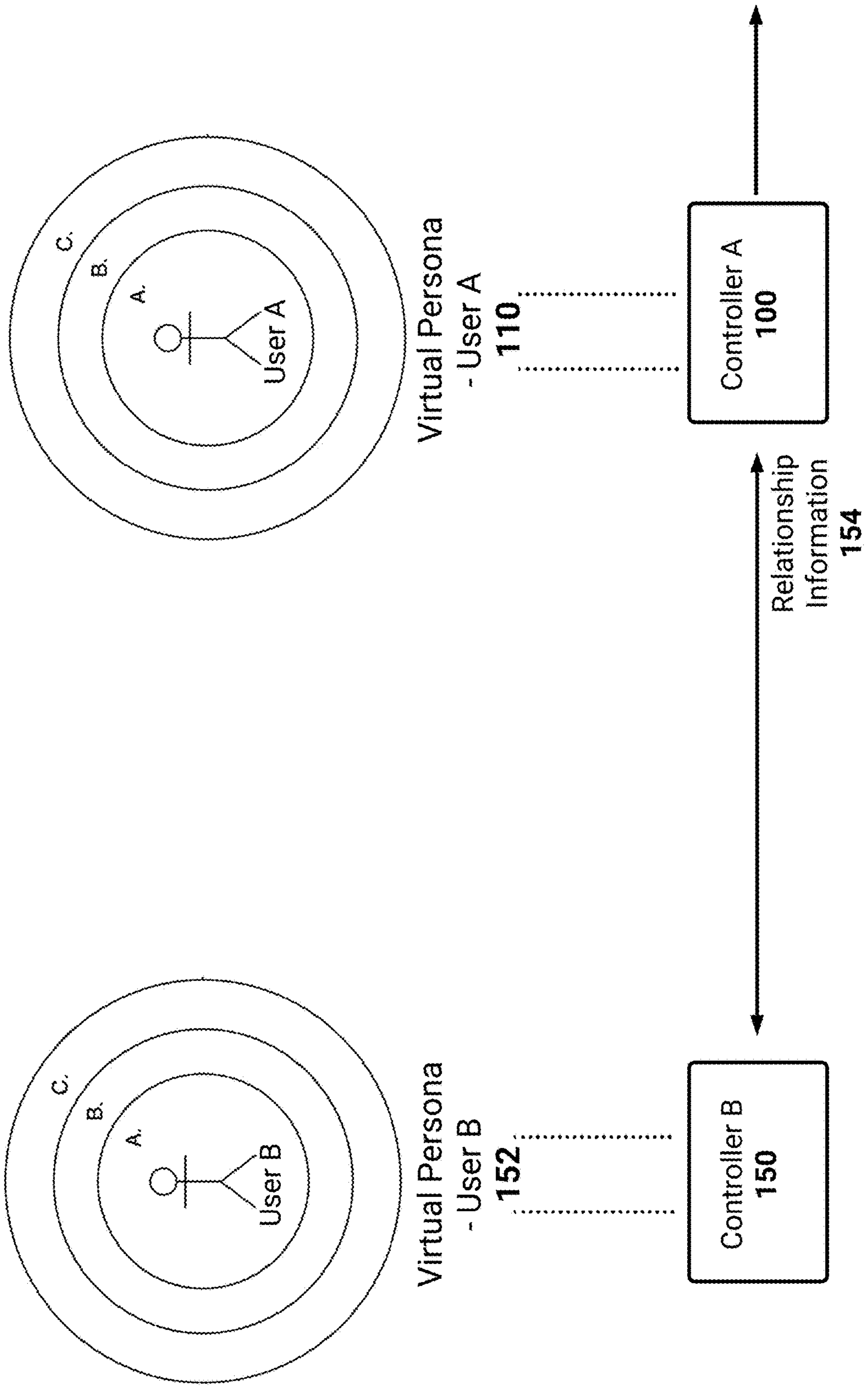
FIG. 1E illustrates the example controller in communication with a different controller associated with a different user.

FIG. 1E illustrates the example controller 100 in communication with a different controller 150 associated with a different user. The different user's virtual persona 152 is illustrated in the example embodiment. As described in FIG. 1A, the user may add one or more friends to indicate relationships to the controller 100.

The relationship information 152 illustrated in FIG. 1E may represent another mesh which is usable by the controller 100. The relationship information 152 may indicate repeating patterns of people who are identified in certain spaces at certain times build the relationship mesh. Optionally, the different user's controller 150 may output one or more confidence metrics associated with the different user. For example, the different controller 150 may provide information to the controller 100 which is generated from the different user's virtual persona 152. The confidence information may therefore reflect a confidence of the controller 150 with respect to the different user's identity. This information may be used by the controller to determine an extent to which the relationship mesh may be trusted. If the different user's identity has a high confidence, then the controller 100 may increase a weight or extent to which the relationship information 154 is used.

Optionally, the relationship information 152 may be utilized by the controller 100 to re-establish the user's identity. As an example, the controller 100 may determine that a confidence in the user's identity is low. As described herein, this may be determined based on less than a threshold number of devices being detected for the environment mesh 114. This may also be determined based on the user not following known behaviors indicated in the behavior mesh 116.

In some embodiments, the user may therefore re-establish trust in the user's identity by the controller. For example, and as described in FIG. 6, the user may provide biometric authentication or may respond to challenge questions. The controller 100 may optionally use the relationship information to re-establish trust. For example, if the controller's 150 confidence in the different user's identity is high, then the controller 100 may optionally increase a confidence in the user's identity. In this example, the different user may represent a partner of the user. Thus, if the partner and the user are both proximate to each other in their house, the controller 100 may re-establish trust.

Example Log-Ins

Figure 2A:
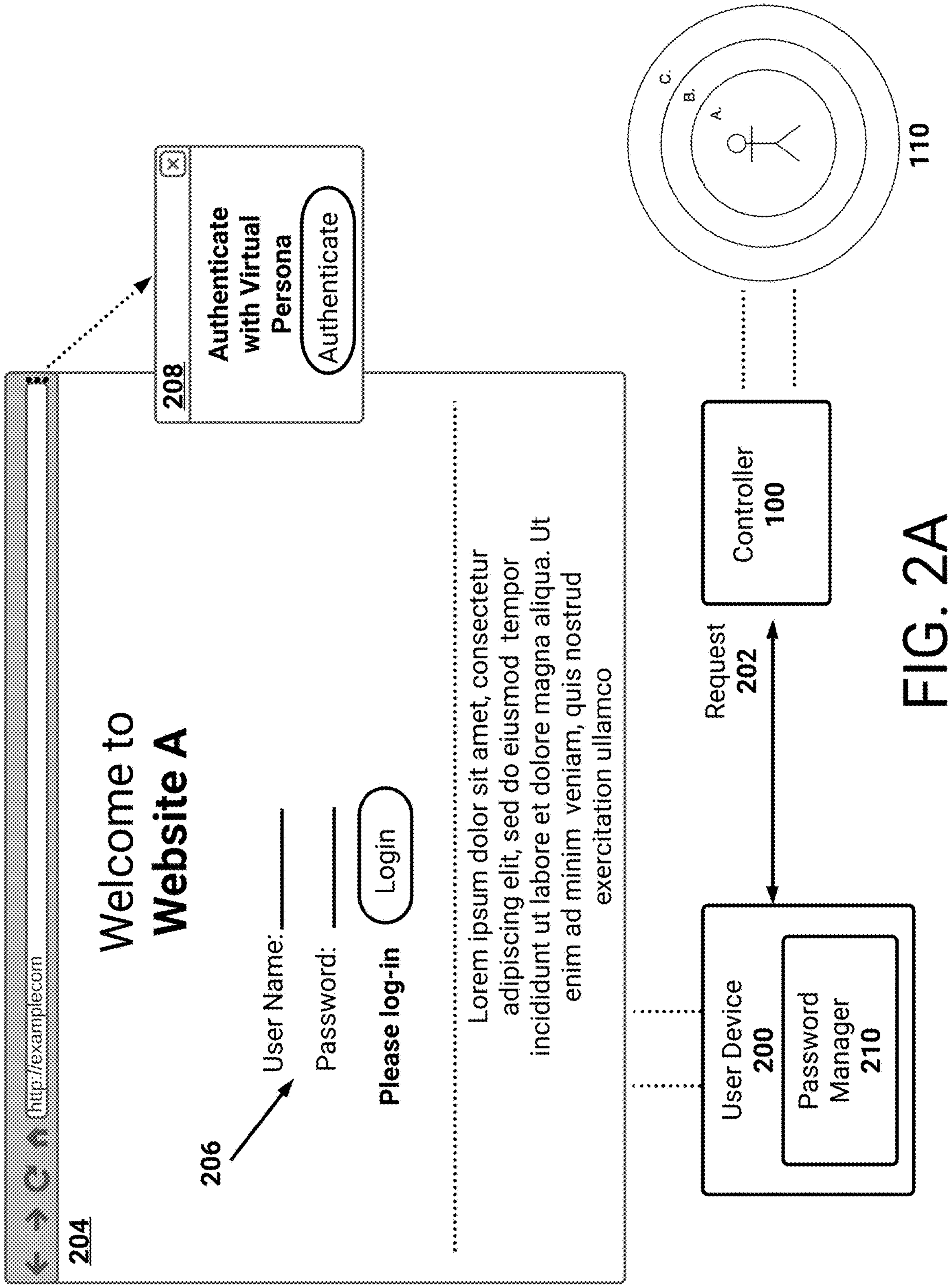
FIG. 2A is a block diagram illustrating the controller receiving a request from a user associated with accessing a website.

FIG. 2A is a block diagram illustrating the controller 100 receiving a request 202 from a user associated with accessing a website 204. In the illustrated embodiment, the controller 100 is maintain a virtual persona 110 associated with the user. The user is accessing the website 204 via a user device 200, such as a mobile device, tablet, laptop, and so on. In the illustrated example, the user device 200 includes a password manager 210 which respond to information from the controller 100.

The website 204 includes a log-in portion 206 in which the user may provide a username and password. In this example, the user may select a button or user interface element to cause presentation of window 208. This window 208 may represent a front-end user interface associated with the password manager 210.

The controller 100 may therefore receive a request 202, for example from the password manager 210, to determine whether a stored username and password associated with the website 204 should be accessed. For example, the controller 100 may represent a smart phone of the user and the controller 100 may receive the request 202 via wireless communication from the user device 200 (e.g., Wi-Fi, Bluetooth). As another example, the request 202 may be provided to an online agent or cloud system which may then route the request 202 to the controller 100. In implementations in which the controller 100 is an online agent, the request 202 may be provided to the online agent (e.g., via an application programming interface, such as to a particular endpoint).

Figure 2B:
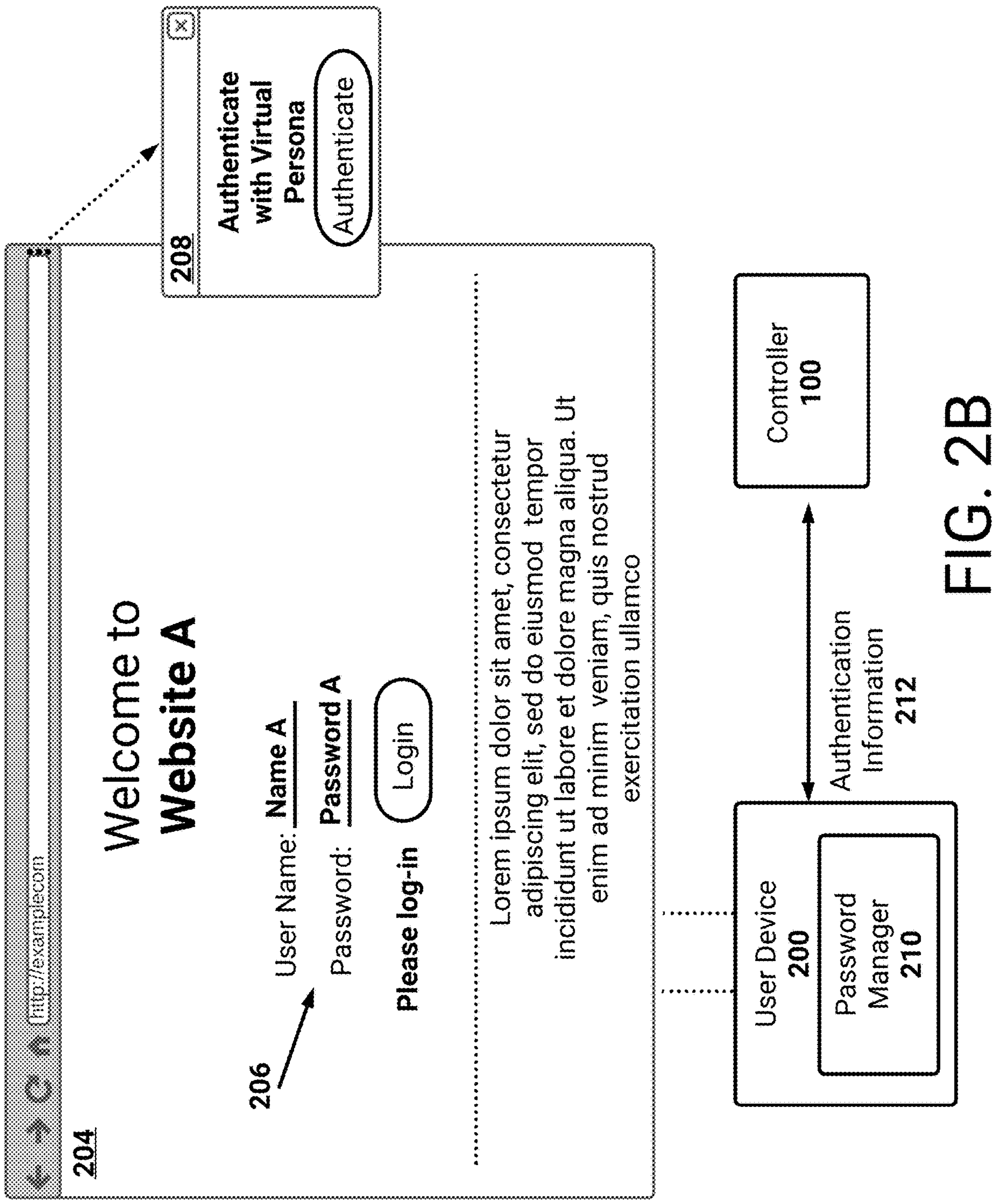
FIG. 2B is a block diagram illustrating the controller authenticating the user based on an associated virtual persona.

FIG. 2B is a block diagram illustrating the controller 100 authenticating the user based on an associated virtual persona 110. In the illustrated example, the controller 100 has determined that one or more confidence metrics in the user's identity exceed one or more thresholds. For example, the controller 100 has determined that the meshes described in FIGS. 2A-2E indicate a high confidence in the user's identity. Thus, the controller 100 has provided authentication information 212 to the password manager 210. Similarly, the password manager 210 has then cause inclusion of a username and password in the log-in portion 206.

As described above, the confidence required to authorize access to the website 204 may be based on a type of information associated with the website. For example, if the website 204 is a banking website, then the controller 100 may require greater confidence. In this example, the controller 100 may require that the virtual persona 110 indicate that greater than a threshold number of devices in the master mesh are presently detectable. The controller 100 may also require that the virtual personal 110 indicate that greater than a threshold number of devices in the environment mesh are presently detectable. These devices may be determined based on a location of the user device 200. The controller 100 may also require that the user carrying the controller and/or user device 200 has followed certain known behaviors identified in the behavior mesh. For example, the controller 100 may determine whether the controller 100 has detected the same Wi-Fi access point names, same vehicle car stereo, and so on, during a commute to the user's present location.

In some embodiments, the controller 100 may periodically cause log-into all systems, software, websites, and so on which are indicated in the password manager. For example, an online agent (described in FIG. 3) may be used to log-onto all websites identified in the password manager. This may be performed based on the controller 100 maintaining a high confidence in the user's identity. This backend access to the websites may allow for the online agent to determine whether the user's passwords have been improperly changed. For example, if the online agent is unable to log-into a website, it may alert the user regarding the improper changing of his/her password. It may also attempt remedial actions automatically. For example, it may try to reset the password, use a backup email address for the user, and so on.

Figure 3:
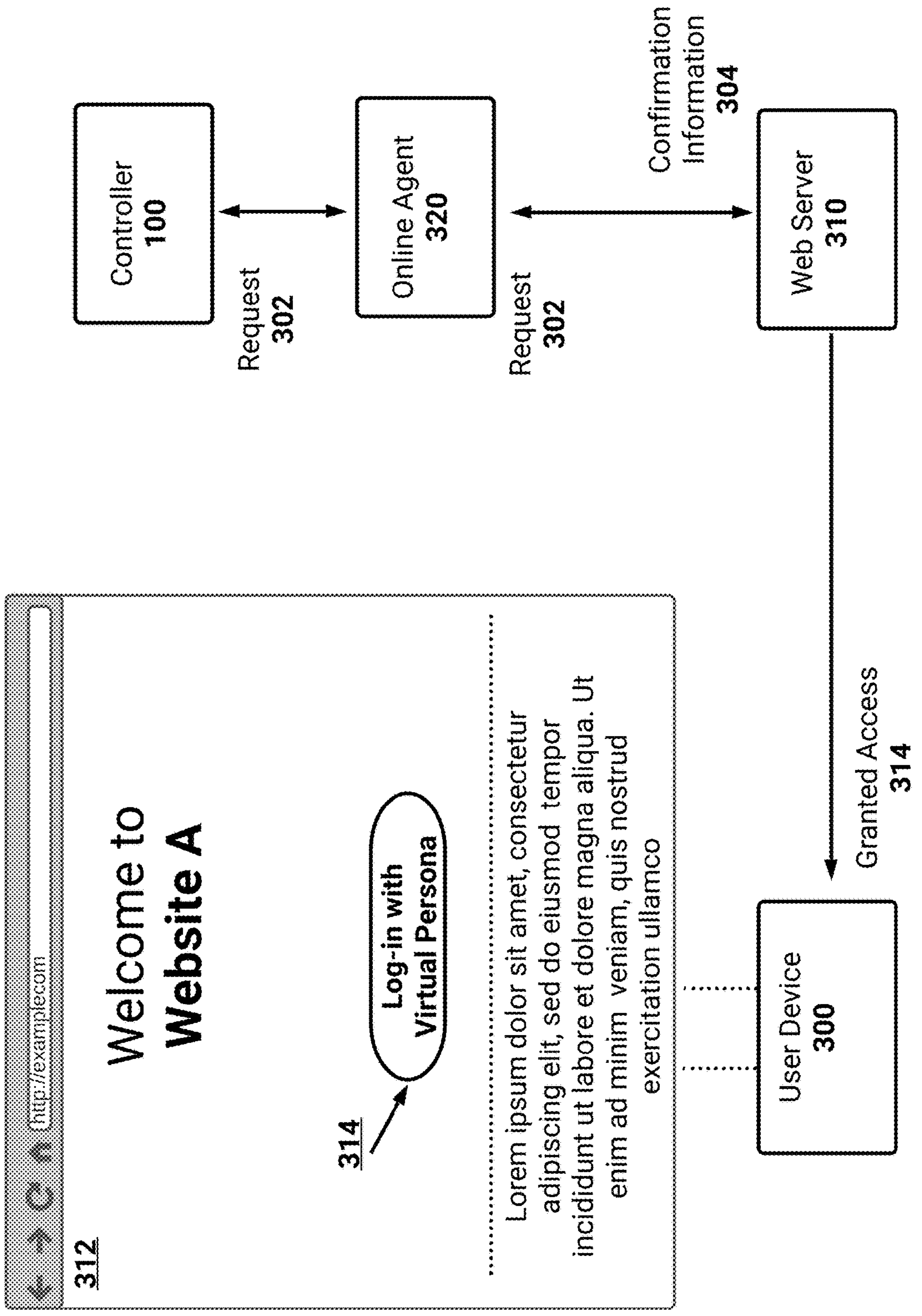
FIG. 3 is a block diagram illustrating the controller in communication with a web server and providing authentication information to the web server.

FIG. 3 is a block diagram illustrating the controller 100 in communication with a web server 310 and providing authentication information 304 to the web server. In some embodiments, an online agent 320 may be used to automatically allow access to a website 312 being presented, at least in part, via a web server 310. The online agent 320 may represent a system of one or more computers which may communicate with one or more controllers via the internet. The online agent 320 may also represent an application or software which is associated with a cloud platform.

In the illustrated example, the website 312 includes a selectable option 314 associated with logging-in via virtual persona. Upon selection of this option 314, the web server 310 may provide a request 302 to the online agent 320 associated with virtual personas. The request 302 may optionally include information indicative of the user device 300. For example, the request 302 may include unique identifying information associated with the device 300 (e.g., a cookie, a MAC address, an IP address, and so on). The request 302 may optionally identify a username associated with the user device 300*s*. For example, the user of the user device 300 may have input a username or a cookie stored on the user device 300 may indicate a username associated with a previous log-in.

The online agent 320 may then analyze the received identifying information and request 302 a controller 100 associated with the user authenticate the user. As an example, the online agent 320 may forward the request 302 to a controller 100 which maintains a virtual persona which has a master mesh that includes the user device 300. In some embodiments, the controller 100 may be part of the online agent 320. In these embodiments, the online agent 320 may therefore perform the functionality described in FIGS. 1A-1E. In some embodiments, the controller may be proximate to the user and the online agent 320 may forward the request 302 over a network (e.g., the internet) to the controller 100.

The controller 100 may determine one or more confidence metrics associated with an identity of a user associated with the controller 100. If the confidence metrics are greater than a threshold, then the online agent may provide confirmation information 304 to the web server 310. The confirmation information 304 may optionally represent a 'thumbs up' or other affirmative information regarding the identity. For example, the confirmation information 304 may represent an event associated with an HMAC-based one-time password algorithm (HOTP). In this way, the online agent 320 may cause the web server to grant access 314 to the website 312.

FIGS. 2A-3 described examples of using a virtual persona to determine authorization to access a website or system (e.g., web server). Similarly, the techniques described herein may allow for a user to automatically access a device (e.g., an internet of things device). As an example, a mobile device may allow for a user to immediately open the mobile device without requiring biometric authentication. As another example, a smart TV platform may allow for the user to effectuate purchases via use of the controller described herein. As another example, a smart speaker may respond to a voice from a user. In this example, the voice may provide a command which may cause access to sensitive information. The controller may therefore receive a request from the smart speaker related to the access. The controller may approve or deny the request based on the user's virtual persona. In this way, the controller may allow for credentials and/or authorization with respect to devices (e.g., internet of things devices).

In some embodiments, an electronic medical record (EMR) system may allow for access by users based on respective virtual personas. For example, a controller may be carried by a user. In this example, the controller may maintain a virtual persona for the user as described herein. The EMR system may optionally detect a presence of the controller when the user sits down at the EMR system. Optionally, the controller may provide information to the EMR system via a wireless connection. Example wireless connections may include a Bluetooth or Wi-Fi connection, or may include a communication via the internet. The EMR system may also allow for the user to enter a username, and the EMR system may provide information to a controller known to be associated with the username (e.g., via online agent 320). The controller may thus authorize the user to access the EMR system based on the user's virtual persona. A level of access may optionally be identified to the EMR system, or determined by the EMR system, based on one or more confidence measures or metrics in the user's identity.

Similarly, in some embodiments the controller or controllers may allow for identity and access management techniques. For example, a healthcare organization may allow for use of virtual personas to enable healthcare IAM. Additionally, virtual persons may be used for healthcare information technology (HIT). For example, online agents may be used to allow for access or authorization to be determined to for HIT systems.

Example Flowcharts

Figure 4A:
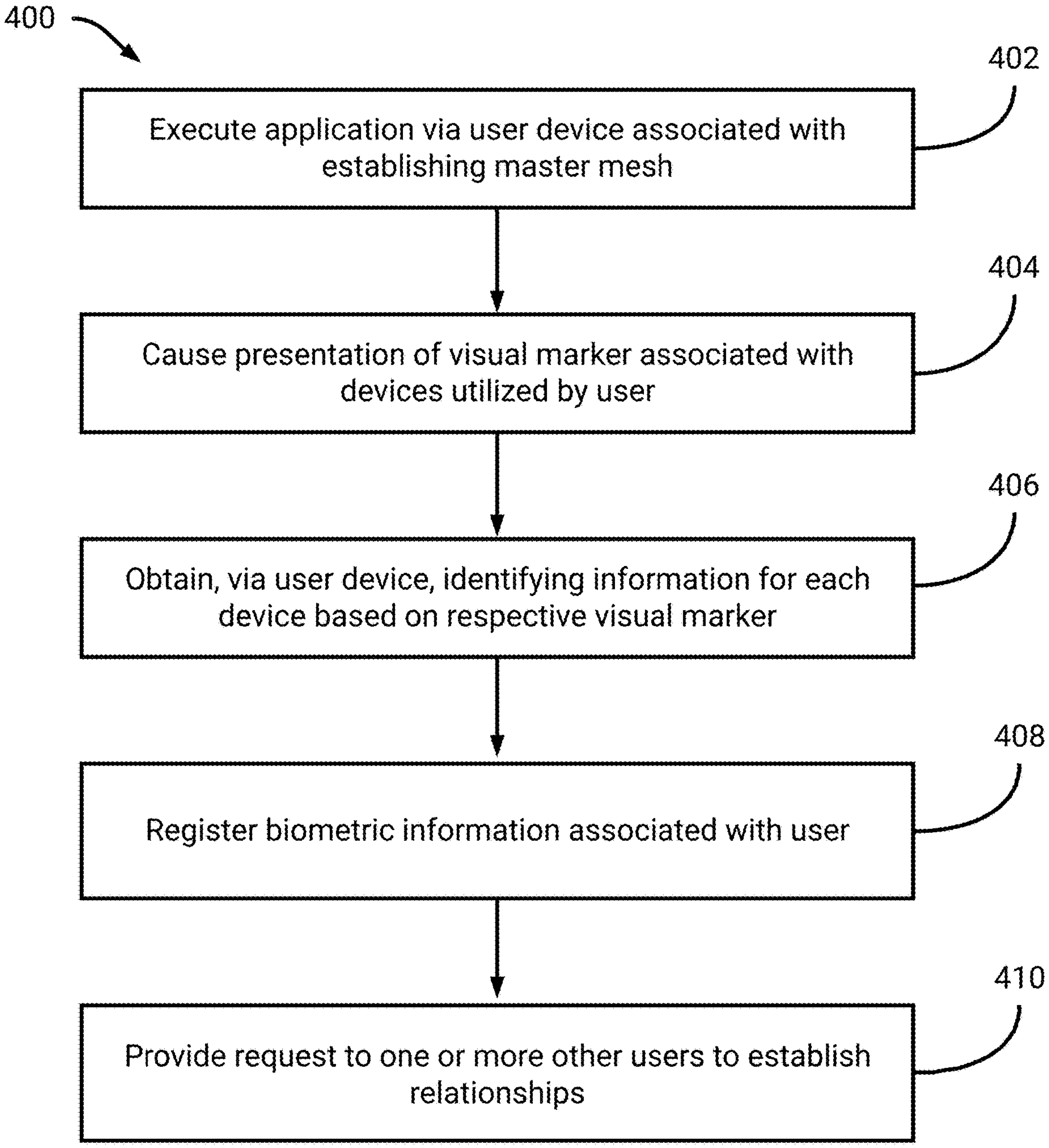
FIG. 4A is a flowchart of an example process for initiating a virtual persona associated with a user.

FIG. 4A is a flowchart of an example process 400 for initiating a virtual persona associated with a user. For convenience, the process 400 will be described as being performed by a controller of one or more processors (e.g., an online agent, a mobile device, a tablet, a wearable device, and so on).

At block 402, the controller executes an application associated with establishing a master mesh. As described in FIG. 1B, the application may be obtained from an online application store.

At block 404, the controller causes presentation of visual markers associated with devices utilized by the user. The controller may detect devices which are proximate to the user. For example, the controller may ping addresses associated with a subset. As another example, devices utilized by the user may similarly execute a same, or similar, application. Additionally, the devices may be navigated to a website or system associated with the controller. For example, a browser on each device may be navigated to a website. As another example, an application may be executed on each device. Thus, the website or application m ay cause presentation of a visual marker which may be associated with the controller. Thus, these devices may output visual markers (e.g., QR codes) which may be analyzed by the controller.

At block 406, the controller obtains identifying information for each device. As described above, the QR code may reflect identifying information (e.g., an IMEI code, a MAC address, and so on). Optionally, the QR code may reflect a time stamp, a location of the device, and.so on.

The controller may obtain this identifying information and use it to generate the master mesh. For example, the master mesh may include the identifying information, or hashes thereof, for these devices. As another example, the master mesh may include other information usable to uniquely identify the devices. For example, particular software running on the devices, particular hardware, and so on, may be used to form a fingerprint of the devices.

At block 408, the controller registers biometric information associated with the user. The controller may require that the user provide biometric information for storage. For example, biometric information may include a thumb print, face scan, voice signature, and so on. This biometric information may be relied upon to confirm the user's identity. For example, and as will be described in FIG. 6, if the controller's confidence in the user's identity is below a threshold, then the controller may require that the user provide biometric information. In this example, the controller may require that the user scan his/her face before authenticating the user to a website, system, and so on.

At block 410, the controller provides a request to one or more users to establish relationships. As described above, the user may add friends to the application. These friends may be used as another mesh or layer to enhance security.

The above-described information may thus be used to initiate a virtual persona for the user. As described in FIG. 4B, additional meshes may be added to the virtual persona. For example, an environment mesh and a behavior mesh may be added.

Figure 4B:
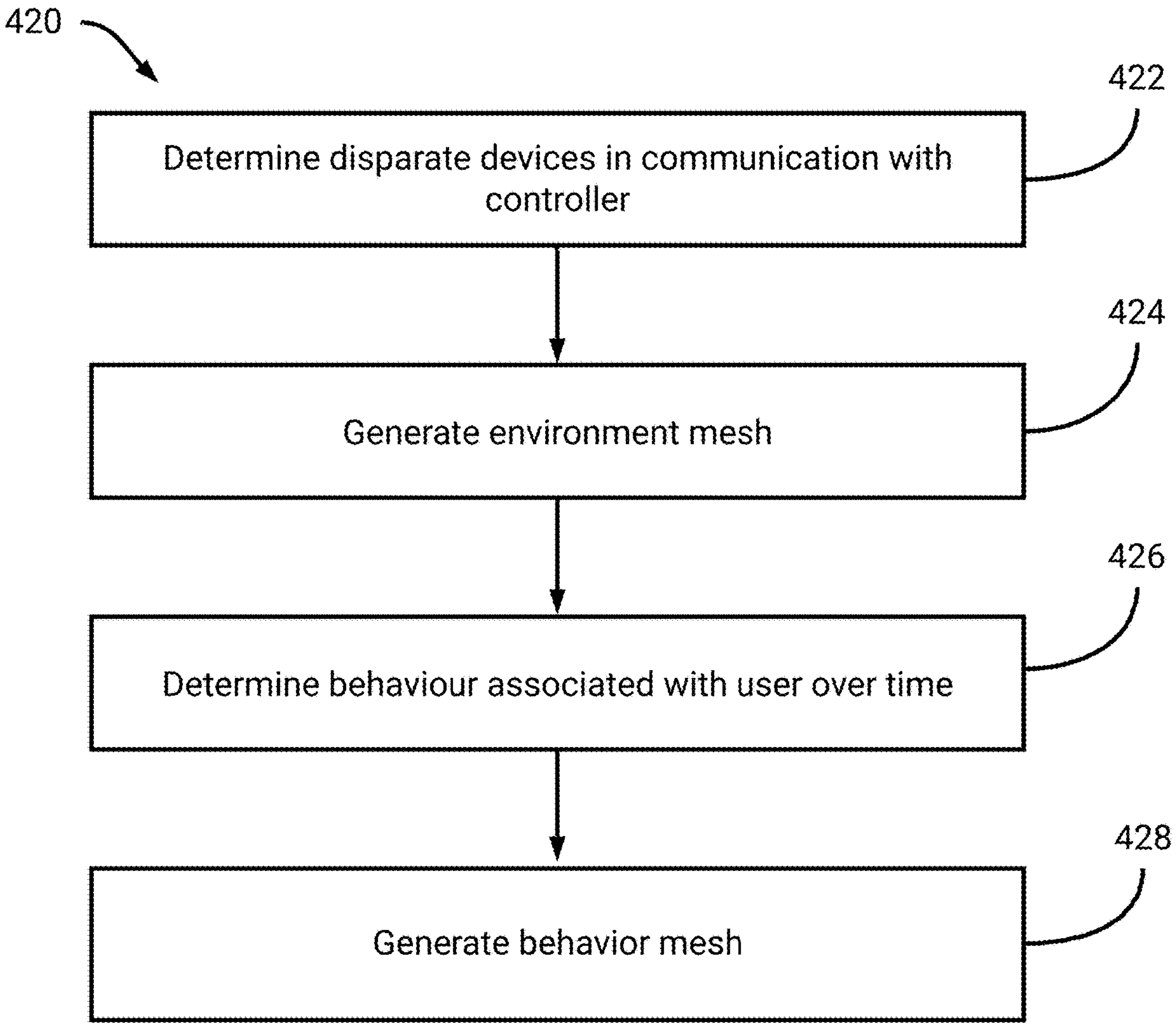
FIG. 4B is a flowchart of an example process for establishing one or more meshes associated with the initiated virtual persona.

FIG. 4B is a flowchart of an example process 420 for establishing one or more meshes associated with the initiated virtual persona. For convenience, the process 420 will be described as being performed by a controller of one or more processors (e.g., an online agent, a mobile device, a tablet, a wearable device, and so on).

At block 422, the controller determines different devices which are in communication with the controller. As described in FIG. 1C, the controller may detect devices within the user's environment. These detected devices may be associated with location information. In this way, the controller may determine that certain devices are detectable at the user's work.

At block 424, the controller generates an environment mesh. The controller may learn specific devices which are to be included in the environment mesh. For example, over a threshold amount of time (e.g., days, weeks) the controller may determine which devices within a user's environment should be included. This may be based on an extent to which the devices are routinely identifiable. As an example, this may be based on an extent to which the devices are fixed in location.

At block 426, the controller determines behavior associated with the user over time, and at block 428 the controller generates the behavior mesh. As described in FIG. 1D, the system may monitor behavior over a threshold amount of time (e.g., weeks, months). In this way, the system may determine routine habits of the user. The system may also determine which devices in the master mesh and environment mesh are implicated by these behaviors. For example, the system may determine that the user typically purchases coffee at a specific coffee shop based on the controller detecting a Wi-Fi access point associated with the coffee shop.

In some embodiments, the behavior mesh may be modified according to real-time occurrences. For example, the user may typically commute to work on a weekday. However, the controller may optionally have access to the user's calendar or email. In this way, the controller may determine that the user has an upcoming meeting which is located at a location different from the user's office. Since the user typically commutes to work, the behavior mesh may indicate a reduced confidence in the user's identity. However, the controller may refute this via the additional information regarding the meeting.

Figure 5:
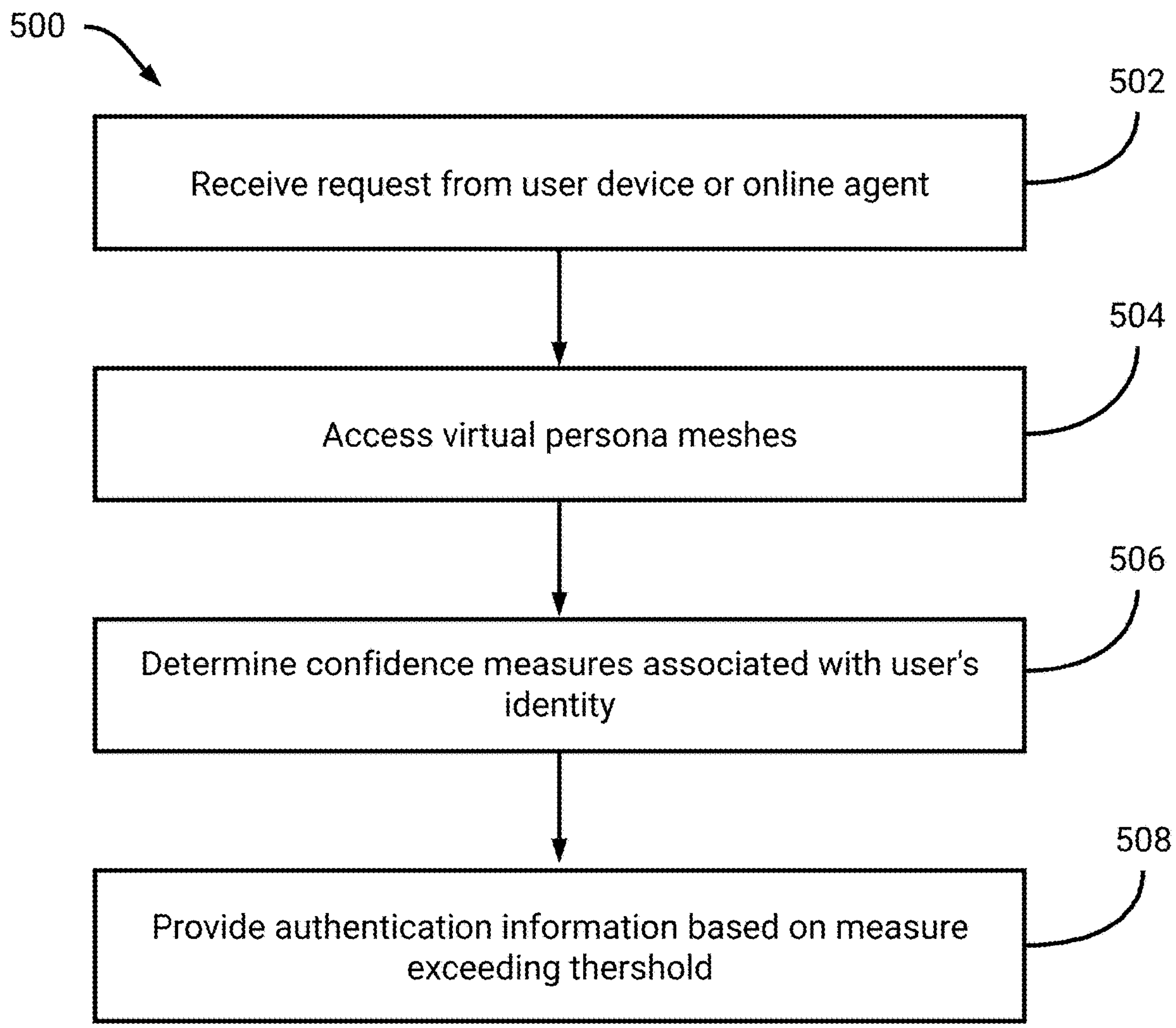
FIG. 5 is a flowchart of an example process for authenticating a user based on confidence measures associated with the user's identity determined from an associated virtual persona.

FIG. 5 is a flowchart of an example process 500 for authenticating a user based on confidence measures associated with the user's identity determined from an associated virtual persona. For convenience, the process 500 will be described as being performed by a controller of one or more processors (e.g., an online agent, a mobile device, a tablet, a wearable device, and so on).

At block 502, the controller receives a request from a user device or online agent to authenticate the user. As described in FIGS. 2A-2B, the user may be attempting to access a website. Thus, the user may prefer that a username and password are automatically included without being required to provide biometric information. The controller may therefore respond to the user device to confirm or deny the user's identity. Additionally, and as described in FIG. 3, the online agent may respond to requests from a web server to authenticate a user on a website. The controller may then provide information to the online agent confirming, or denying, the user's identity.

At block 504, the controller accesses a virtual persona. The controller may access the meshes included in the virtual persona, for example as described above.

At block 506, the controller determines confidence measures associated with the user's identity. As described above, the controller may determine one or more confidence measures. The confidence measures may be based on a number of features associated with each mesh. With respect to the master mesh, a confidence measure may be based on a number of features (e.g., devices) which are proximate to the user or which were proximate within a threshold amount of time. With respect to the environment mesh, a confidence measure may be based on a number of detectable devices known to be associated with the environment mesh. For example, the confidence measure may indicate that there are a threshold number of known devices on a particular network and/or there are a threshold number of known devices which were recently detected (e.g., a car stereo while the user was driving to work). With respect to the behavior mesh, a confidence measure may be based on information regarding behavior. For example, a measure may be based on how closely the user is following a particular routine based on timestamps associated with locations of the user. In this example, historical location information be compared with present location of the user. Thus, if the user commonly leaves the house at a similar time, reaches a coffee shop at a similar time, and so on, (e.g., via comparisons to timestamps), then the confidence may be increased. Optionally, the controller may use machine learning techniques to determine the confidence measures, or an overall likelihood associated with the user's identity.

At block 508, the controller provides authentication information in response. The controller may determine that the confidence measures exceed one or more thresholds. Thus, the controller may provide information to the user device authenticating the user. The user device may then provide a username and password to the website. With respect to an online agent, the online agent may provide confirmation information to a web server. The web server may then allow access to the website. Optionally, the controller may maintain OAuth or HOTP authentication information associated with websites, servers, devices, and so on. Thus, the controller may provide encrypted information (e.g., encrypted keys, access tokens, or other information) which is usable to allow access.

Figure 6:
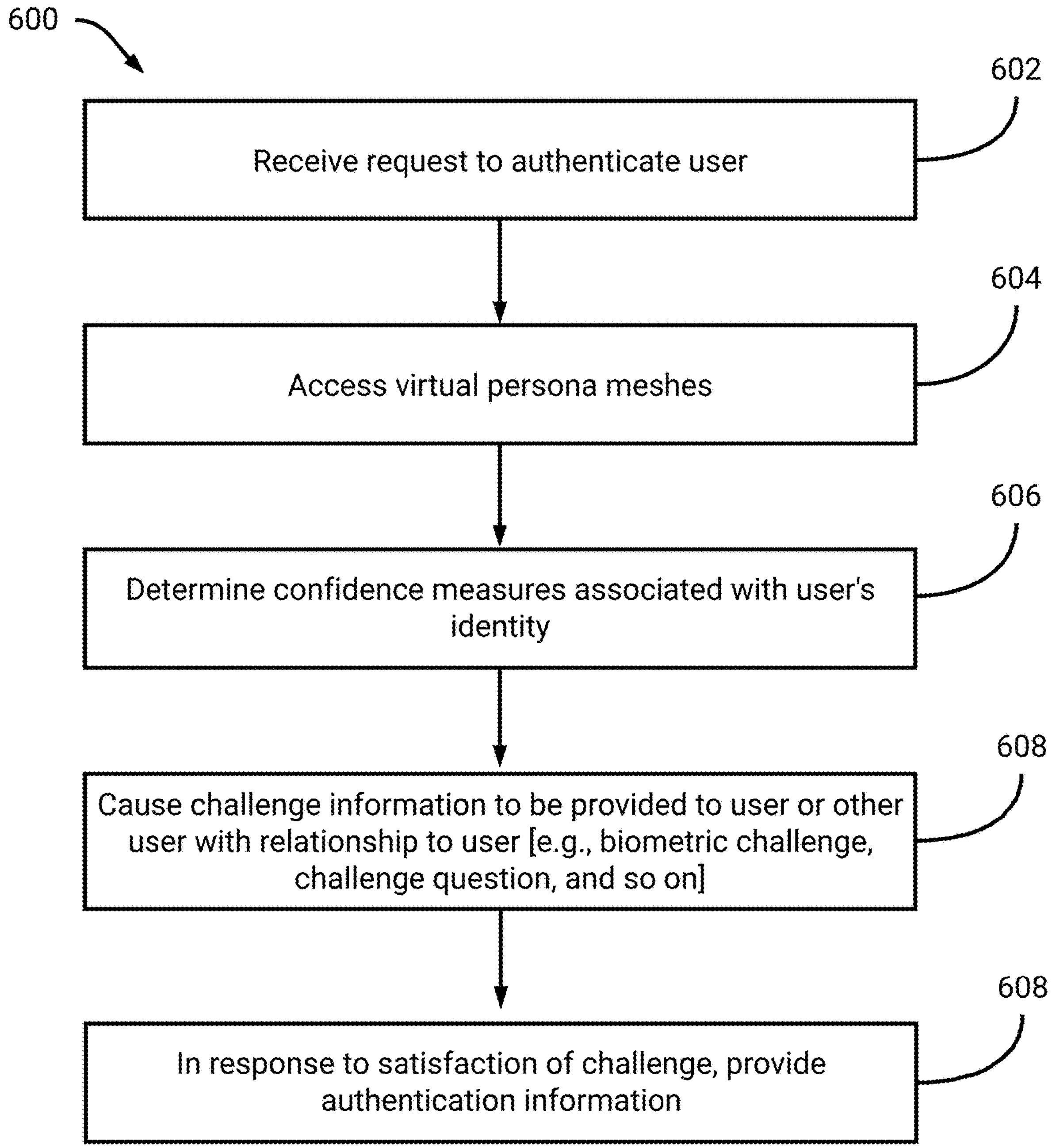
FIG. 6 is a flowchart of an example process for providing challenge information to a user based on confidence measures being less than one or more threshold metrics.

FIG. 6 is a flowchart of an example process 600 for providing challenge information to a user based on confidence measures being less than one or more threshold metrics. For convenience, the process 600 will be described as being performed by a controller of one or more processors (e.g., an online agent, a mobile device, a tablet, a wearable device, and so on).

At block 602, the controller receives a request to authenticate the user. At block 604, the controller accesses a virtual persona of the user. At block 606, the controller determines confidence measures.

At block 608, the controller causes challenge information to be provided to the user. For example, if the confidence measures are below a threshold, the controller may not have sufficient confidence in the user's identity. Thus, the controller may require that the user provide additional information. Example information may include requiring that the user provide biometric information to the controller. For example, the user may be required to place his/her thumb on a thumbprint reader of the controller or on a mobile device included in the master mesh. The user may also be required to answer a challenge question. For example, the controller may ask personal information of the user (e.g., who are your friends, where were you last Saturday, and so on). The user may also be required to bring his/her Bluetooth badge up to the controller or a mobile device. This may allow the controller to scan the Bluetooth badge.

In some embodiments, the controller may leverage relationship information. As described in FIG. 4A, the user may identify friends of the user who are also using the virtual persona techniques described herein. The controller may, as an example, cause a smart speaker on the user's network to the user's nearby friend to speak out loud a key phrase shown on the user's mobile device.

At block 610, the controller may provide authentication information. Upon satisfaction of the challenge information, the controller may authenticate the user.

Figure 7:
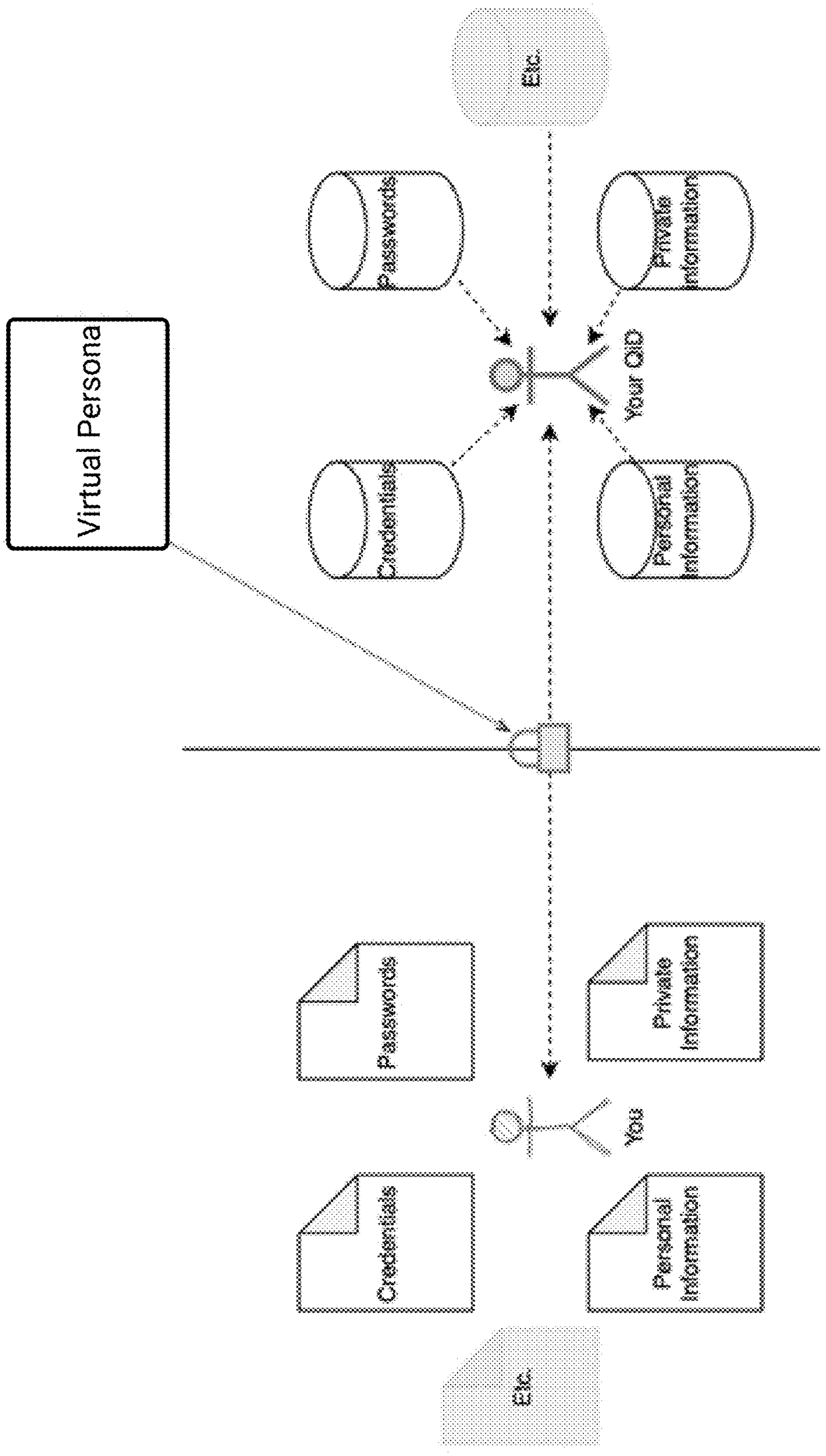
FIG. 7 is a block diagram illustrating digital twinning which leverages a virtual persona.

FIG. 7 is a block diagram illustrating digital twinning which leverages a virtual persona. In some embodiments, a virtual persona and/or controller may be used for a digital representation of a user. In the illustrated example, the QiD may represent a digital representation of a user and handle security profiles around certain types of information. QiD is able to autonomously use information of a certain security profile. For example, certain personal information might be share with trusted relations (biometrics with healthcare providers for instance)/other information such as private information may never be shared without the user's active consent. The certain personal information may be shared based on a controller or controller determining that one or more confidence metrics or measures associated with the user's identity exceed one or more thresholds. Optionally, the trust relations may only receive the information if their controller or controllers determine that confidence metrics or measures associated with their identities exceed one or more thresholds.

The description herein described the controller or controllers determining information. As described in FIG. 3, in some embodiments one or more online agents may determine confidence measures or metrics. Thus, portions of this application which describe the controller determining information may be understood to additionally describe the controller or controller determining information.

Figure 8A:
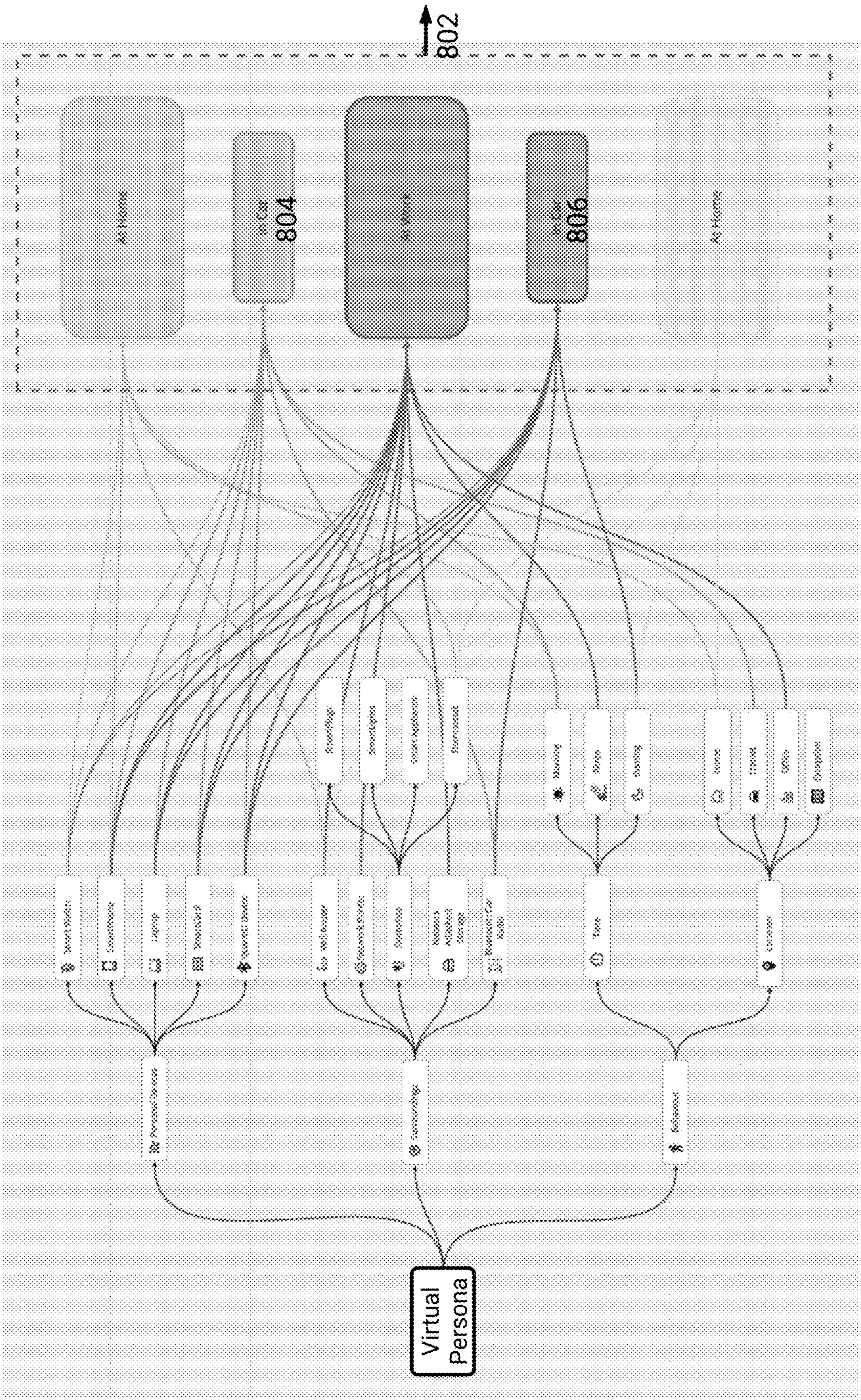
FIGS. 8A-8B are block diagrams illustrating example information usable to establish a virtual persona.

FIG. 8A is a block diagram illustrating example information usable to establish a virtual persona. As illustrated, personal devices, surroundings (e.g., environment), and behavior, information is depicted. These each are associated with different devices, times, and/or locations. For example, 'car' 804 is illustrated as being associated with a smartwatch, smartphone, laptop, smartcard, Bluetooth car radio, time of day (e.g., morning), and location (e.g., 'transit'). Car 806, which may represent use of the car at a different time, is similarly associated with smartwatch, smartphone, laptop, smartcard, Bluetooth car radio, time of day (e.g., evening), and location (e.g., 'transit'). This information 802 may thus be used to form the meshes described herein.

Figure 8B:
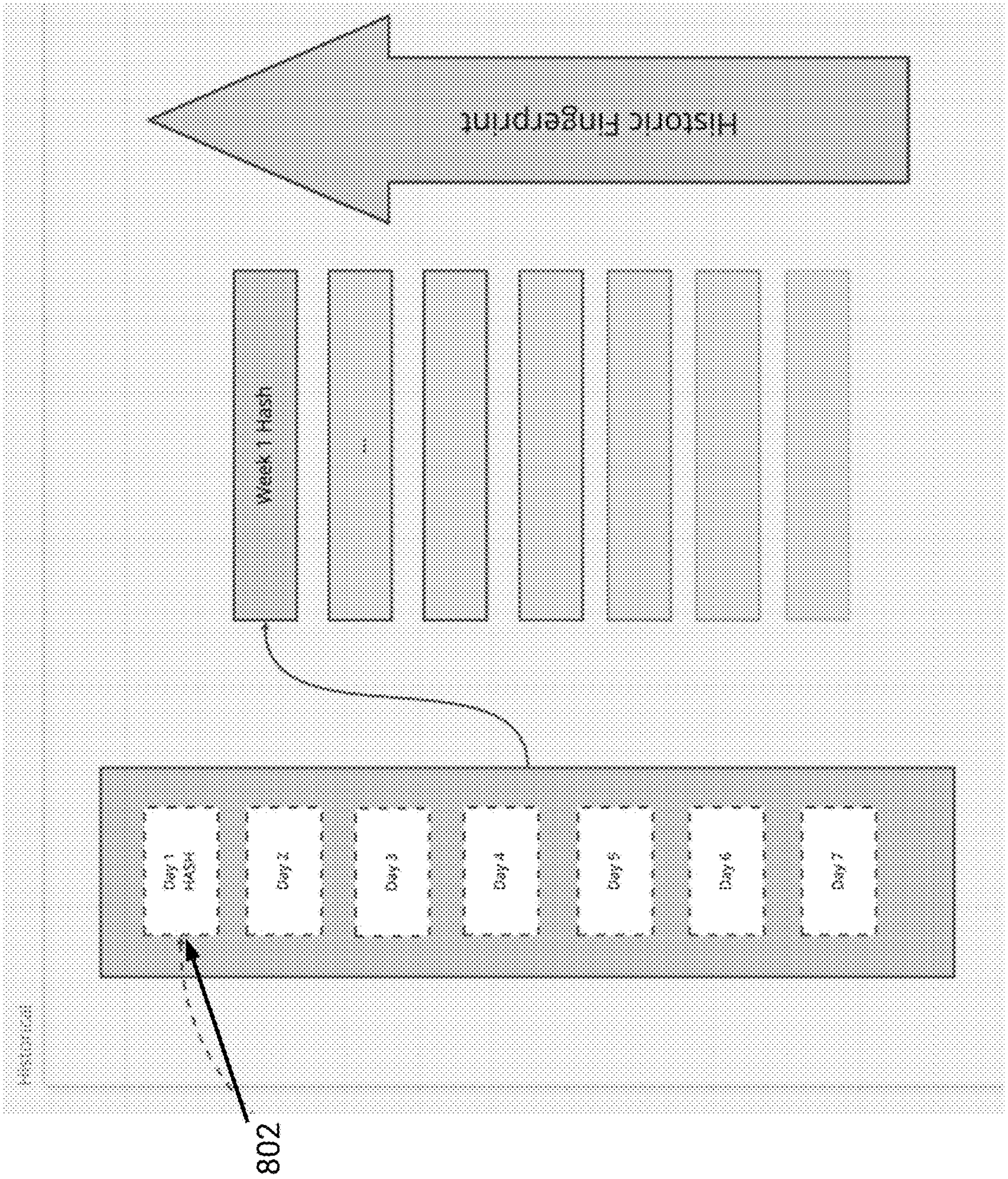

FIG. 8B is a block diagram illustrating example information usable to establish a virtual persona. In the illustrated example, the information 802 aggregated in FIG. 8A is associated with a particular day (e.g., Day 1). This information may be hashed or otherwise stored. Additionally, the information may be aggregated over the week and then hashed again or otherwise stored ('week 1 hash'). Thus, overtime historical information associated with the user may be determined. In this way, the meshes may be stablished and used to determine a confidence in an identity of a user. For example, current information may be compared to this historical information. In this example, and with respect to a car, a controller may determine that the smartwatch, smartphone, laptop, smartcard, Bluetooth car and/or radio are present during the car ride. Additionally, the controller may compare the time of day to historical times of days. Additionally, the controller may compare an ending location (e.g., work) to known ending locations. In this way, the confidence in the identity may be determined.

Additional Embodiments

All of the processes described herein may be embodied in, and fully automated, via software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence or can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A method comprising:

obtaining information identifying a plurality of devices associated with a user, wherein individual devices included in a first subset of the devices execute an application which is configured to communicate with a controller proximate to a user, and wherein the individual devices are identified by the controller according to identifying information which is hashed and stored in the controller, wherein individual devices included in a second subset of the devices are responsive to wired or wireless communications with the controller and are associated with locations; and generating a plurality of meshes based on the information, the meshes comprising:

a master mesh associated with the first subset of devices; and an environment mesh associated with the second subset of devices; and responding to an authorization request associated with the user based upon a confidence metric based upon the plurality of meshes, wherein responding to the authorization request associated with the user based upon the confidence metric comprises allowing the user to access a specific website based on a threshold level of confidence being met.

2. The method of claim 1, wherein the application, when executed by the controller and the first subset of devices, causes the first subset of devices to present a visual marker which is identified by the controller as being associated with the user.

3. The method of claim 2, wherein the visual marker is a quick-response (QR) code.

4. The method of claim 3, wherein associating the visual marker with the user comprises hashing and storing the information of the QR code.

5. The method of claim 1, wherein the second subset of the devices are identified over a threshold amount of time as being associated with the user.

6. The method of claim 5, wherein the second subset of devices are identified according to identifying information which is hashed and stored based on an extent to which the identifying information is routinely identified over the threshold amount of time.

7. The method of claim 1, wherein a device of the second subset of devices is associated with a location when the device is identified at the location a threshold number of instances.

8. The method of claim 1, wherein responding to the authorization request based upon the confidence metric further comprises allowing the user to access a piece of specific information based on a particular threshold level of confidence being met.

9. A system comprising one or more processors and non-transitory computer storage media storing instructions that when executed by the one or more processors, cause the one or more processors to perform operations comprising:

obtaining information identifying a plurality of devices associated with a user, wherein individual devices included in a first subset of the devices execute an application which is configured to communicate with a controller proximate to a user, and wherein the individual devices are identified by the controller according to identifying information which is hashed and stored in the controller, wherein individual devices included in a second subset of the devices are responsive to wired or wireless communications with the controller and are associated with locations; and generating a plurality of meshes based on the information, the meshes comprising:

a master mesh associated with the first subset of devices; and an environment mesh associated with the second subset of devices; and responding to the authorization request associated with the user based upon a confidence metric based upon the plurality of meshes, wherein responding to the authorization request comprises allowing the user to access a website based on a threshold level of confidence being met.

10. The system of claim 9, wherein the application, when executed by the controller and the first subset of devices, causes the first subset of devices to present a visual marker which is identified by the controller as being associated with the user.

11. The system of claim 10, wherein the visual marker is a quick-response (QR) code.

12. The system of claim 11, wherein associating the visual marker with the user comprises hashing and storing the information of the QR code.

13. The system of claim 9, wherein the second subset of the devices are identified over a threshold amount of time as being associated with the user.

14. The system of claim 13, wherein the second subset of devices are identified according to identifying information which is hashed and stored based on an extent to which the identifying information is routinely identified over the threshold amount of time.

15. The system of claim 9, wherein a device of the second subset of devices is associated with a location when the device is identified at the location a threshold number of instances.

16. The system of claim 9, wherein responding to the authorization request based upon the confidence metric further comprises allowing the user to access a piece of specific information based on a particular threshold level of confidence being met.

17. Non-transitory computer storage media storing instructions that when executed by a system of one or more computers, cause the one or more computers to perform operations comprising:

obtaining information identifying a plurality of devices associated with a user, wherein individual devices included in a first subset of the devices execute an application which is configured to communicate with a controller proximate to a user, and wherein the individual devices are identified by the controller according to identifying information which is hashed and stored in the controller, wherein individual devices included in a second subset of the devices are responsive to wired or wireless communications with the controller and are associated with locations; and generating a plurality of meshes based on the information, the meshes comprising:

a master mesh associated with the first subset of devices; and an environment mesh associated with the second subset of devices; and responding to an authorization request associated with the user based upon a confidence metric based upon the plurality of meshes, wherein responding to the authorization request comprises allowing the user to access a website based on a threshold level of confidence being met.

18. The computer storage media of claim 17, wherein responding to the authorization request based upon the confidence metric further comprises allowing the user to access a piece of specific information based on a particular threshold level of confidence being met.

* * * * *